US008771599B2

(12) United States Patent
Funabiki et al.

(10) Patent No.: US 8,771,599 B2
(45) Date of Patent: Jul. 8, 2014

(54) ION DETECTING APPARATUS AND ION GENERATING APPARATUS

(75) Inventors: Fumimasa Funabiki, Osaka (JP); Tomohisa Itoh, Osaka (JP); Yoshihiro Uramoto, Osaka (JP); Takahiro Hanai, Osaka (JP); Yoshiroh Tanoue, Osaka (JP)

(73) Assignee: Sharp Kabushiki Kaisha, Osaka (JP)

( * ) Notice: Subject to any disclaimer, the term of this patent is extended or adjusted under 35 U.S.C. 154(b) by 483 days.

(21) Appl. No.: 13/061,094

(22) PCT Filed: Mar. 17, 2009

(86) PCT No.: PCT/JP2009/055140
§ 371 (c)(1),
(2), (4) Date: Feb. 25, 2011

(87) PCT Pub. No.: WO2010/023979
PCT Pub. Date: Mar. 4, 2010

(65) Prior Publication Data
US 2011/0155922 A1    Jun. 30, 2011

(30) Foreign Application Priority Data

Aug. 28, 2008  (JP) ................................. 2008-220325
Aug. 28, 2008  (JP) ................................. 2008-220328
Aug. 28, 2008  (JP) ................................. 2008-220330

(51) Int. Cl.
*G05B 17/00*         (2006.01)
(52) U.S. Cl.
USPC ........................... 422/116; 422/119; 422/121

(58) Field of Classification Search
USPC .............. 422/22, 108, 119, 121, 5, 105, 116, 422/120; 250/423 R–423 F
See application file for complete search history.

(56) References Cited

U.S. PATENT DOCUMENTS 3,217,470 A      11/1965  Omohundro
5,893,977 A *    4/1999   Pucci .............................. 422/22
(Continued)

FOREIGN PATENT DOCUMENTS

EP       1671659 A1    6/2006
JM       2005-100870 A 4/2005
(Continued)

OTHER PUBLICATIONS

U.S. Office Action for co-pending U.S. Appl. No. 13/259,240 dated Jun. 7, 2013.

(Continued)

*Primary Examiner* — Timothy Cleveland
(74) *Attorney, Agent, or Firm* — Birch, Stewart, Kolasch & Birch, LLP

(57) ABSTRACT

An air blower including a motor 2 having output shafts 21, 21 on both sides in the axial direction and two impellers 3, 3 mounted on the respective output shafts 21, 21, and two ducts 5, 5 that individually allow passage of the air blown out by rotation of each of the impellers 3, 3 in the same direction and discharge the air to the outside are included. At a part or the whole of each of the ducts 5, 5, a laminar flow section that makes the flowing air laminar flow. An ion generating section is arranged at each laminar flow section so that ions generated by the ion generating section can effectively be included in the air, increasing the ion concentration of ions discharged in a room together with the air.

6 Claims, 27 Drawing Sheets

(56) References Cited

U.S. PATENT DOCUMENTS

| | | |
|---|---|---|
| 7,397,647 B2 | 7/2008 | Mizuno et al. |
| 2004/0218315 A1 | 11/2004 | Mizuno et al. |
| 2005/0163669 A1* | 7/2005 | Taylor et al. .................. 422/121 |
| 2005/0287051 A1* | 12/2005 | Yuen .......................... 422/186.3 |
| 2006/0024197 A1 | 2/2006 | Park et al. |
| 2006/0279897 A1 | 12/2006 | Mizuno et al. |
| 2007/0274019 A1 | 11/2007 | Nakajima |
| 2008/0138242 A1 | 6/2008 | Park et al. |
| 2008/0252189 A1 | 10/2008 | Regan |
| 2011/0155922 A1 | 6/2011 | Funabiki et al. |

FOREIGN PATENT DOCUMENTS

| | | |
|---|---|---|
| JP | 3-266398 A | 11/1991 |
| JP | 7-37383 U | 7/1995 |
| JP | 8-62180 A | 3/1996 |
| JP | 3048869 U | 5/1998 |
| JP | 11-304356 A | 11/1999 |
| JP | 2002-78788 A | 3/2002 |
| JP | 2002-352997 A | 12/2002 |
| JP | 2004-3885 A | 1/2004 |
| JP | 2004-87493 A | 3/2004 |
| JP | 2005-61950 A | 3/2005 |
| JP | 2005-76906 A | 3/2005 |
| JP | 2005-116229 A | 4/2005 |
| JP | 2005-147455 A | 6/2005 |
| JP | 2005-214463 A | 8/2005 |
| JP | 2005-328904 A | 12/2005 |
| JP | 2005-339935 A | 12/2005 |
| JP | 2006-35204 A | 2/2006 |
| JP | 3770784 B2 | 4/2006 |
| JP | 2006/106594 A1 | 10/2006 |
| JP | 2007-114177 A | 5/2007 |
| JP | 2007-242389 A | 9/2007 |
| JP | 2007-294180 A | 11/2007 |
| WO | WO 03/098759 A1 | 11/2003 |
| WO | WO 2007/131981 A1 | 11/2007 |
| WO | WO 2010/023979 A1 | 3/2010 |

OTHER PUBLICATIONS

Extended European Search Report for European Application No. 10755745.6 dated Nov. 5, 2012.

International Search Report for International Application No. PCT/JP2010/051218 dated Apr. 6, 2010.

U.S. Notice of Allowance issued in co-pending U.S. Appl. No. 13/259,240, dated Nov. 27, 2013.

* cited by examiner

F I G. 1 2
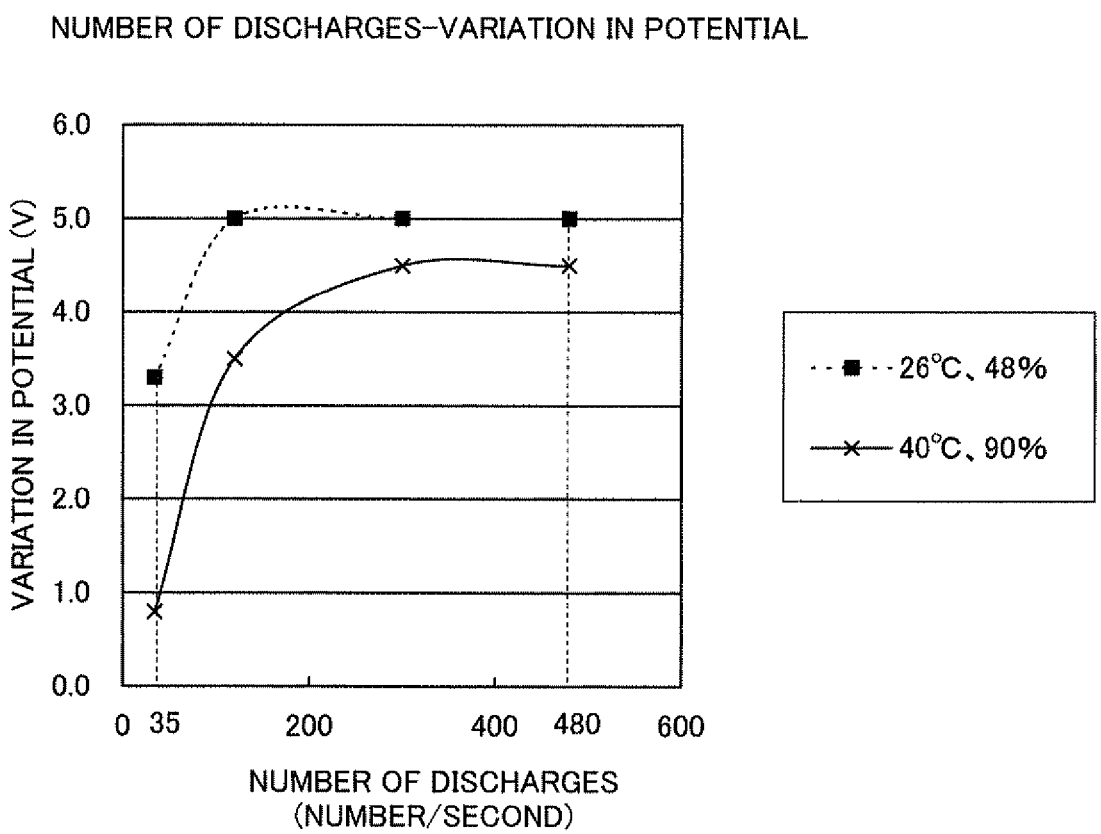

FIG. 27

| CASE | ARRANGEMENT & POLARITY | NUMBER OF USES | ENERGIZED TIME | COMBINATION OF ALTERNATING ON/OFF | AVERATE ION CONCENTRATION (NUMBER OF IONS/CM³) | |
|---|---|---|---|---|---|---|
| | | | | | POSITIVE ION | NEGATIVE ION |
| 1 | -A+ +B- | 2 | CONSTANTLY ON | — | 54000 | 52800 |
| 2 | -A+ +B- | 2 | ON/OFF FOR 1 SEC | ALTERNATELY A/B | 39100 | 38800 |
| 3 | -A+ -B+ +C- +D- | 4 | ON/OFF FOR 1 SEC | ALTERNATELY A, B/C, D (A, B IN THE SAME PHASE, C, D IN THE SAME PHASE) | 40000 | 32000 |
| 4 | -A+ +B+ +C+ +D- | 4 | ON/OFF FOR 1 SEC | SAME AS ABOVE | 50000 | 20000 |
| 5 | +A- -B+ +C- -D+ | 4 | ON/OFF FOR 1 SEC | ALTERNATELY A, D/B, C (A, D IN THE SAME PHASE, B, C IN THE SAME PHASE) | 52000 | 52400 |

US 8,771,599 B2

ION DETECTING APPARATUS AND ION GENERATING APPARATUS

This application is the National Phase of PCT/JP2009/055140 filed on Mar. 17, 2009, which claims priority under 35 U.S.C. 119(a) to Patent Application Nos. 2008-220325, 2008-220328 and 2008-220330 filed in Japan on Aug. 28, 2008, all of which are hereby expressly incorporated by reference into the present application.

TECHNICAL FIELD

The present invention relates to an ion detecting apparatus that detects ions in the air and to an ion generating apparatus including the ion detecting apparatus.

BACKGROUND ART

In a residential room, bacteria, virus and the like such as serratia and bacillus are floating while unpleasant odors are attached to curtains, clothes and the like hung in the room. An air purifier is provided in such a room in order to clean the air in the room. The air purifier described in Patent Document 1 includes dielectrics that generate $H^+(H_2O)_n$ of a positive ion and $O_2^-(H_2O)_n$ of a negative ion, and an air blower that discharges $H^+(H_2O)_n$ and $O_2^-(H_2O)_n$ generated by the dielectrics in a room.

The air purifier generates $H^+(H_2O)_n$ and $O_2^-(H_2O)_n$ at the same time to produce hydrogen peroxide $H_2O_2$ or hydroxyl radical (.OH), which are active species, by chemical reaction. Since the hydrogen peroxide $H_2O_2$ or hydroxyl radical (.OH) shows extremely high activity, floating bacteria may be decomposed and eliminated by discharging the hydrogen peroxide $H_2O_2$ or hydroxyl radical (.OH) in the air in a room.

In recent years, a technique of purifying the air in a residential space by charging water molecules in the air with positive (plus) and/or negative (minus) ions has widely been used. For example, an ion generating apparatus represented by an air purifier is provided with an ion generator that generates positive and negative ions along the path of the inside air-flowing path to discharge the generated ions to the outside space together with the air.

In a residential space, the ions charging the water molecules in the clean air inactivates floating particles and killing floating bacteria while degenerating odor components to purify the air in the entire residential space.

A standard ion generator generates corona discharge to generate positive and negative ions by applying a driving voltage, which is a high and alternating voltage, between a needle electrode and an opposite electrode or between a discharge electrode and a dielectric electrode.

When, however, the ion generator is used for a prolonged period and thus the discharge electrode is worn out due to sputter evaporation associated with corona discharge, or when foreign materials such as chemicals, dust and the like are cumulatively attached to the discharge electrode, decrease in the amount of generated ions cannot be avoided. Here, it is required to detect ions in the air in order to notify the user that the ion generator needs maintenance.

To address the above, for example, Patent Document 2 discloses an ion sensor provided with an electrode that collects ions in the air to detect ions.

In recent years, a technique of purifying the air in a residential space by charging water molecules in the air with positive (plus) and/or negative (minus) ions has widely been used. For example, an ion generating apparatus represented by an air purifier is provided with an ion generator that generates positive and negative ions along the path of the inside air-flowing path to discharge the generated ions to the outside space together with the air.

In a residential space, the ions charging the water molecules in the clean air inactivates floating particles and killing floating bacteria while denaturing odor components to purify the air in the entire residential space.

A standard ion generator causes corona discharge to generate positive and negative ions by applying a driving voltage, which is a high and alternating voltage, between a needle electrode and an opposite electrode or between a discharge electrode and a dielectric electrode.

For example, with the air purifier disclosed in Patent Document 1, the concentration of ions discharged with the air corresponds to 1000 to 2000/cm$^3$ in a normal room. Thus, a certain level of sterilization effects on bacteria such as serratia and bacillus may be expected. However, the effects of eliminating virus and of eliminating odor attached to curtains, clothes and the like are small. An ion generating apparatus that can increase the ion concentration in a room has been desired.

Moreover, since one ion generator may generate only a limited amount of ions, an attempt has been made in which a plurality of ion generators are arranged in an air-flowing path to increase the amount of generated ions.

[Patent Document 1] Japanese Patent Publication No. 3770784

[Patent Document 2] Japanese Patent Application Laid-open No. 2004-3885

DISCLOSURE OF THE INVENTION

Problems to be Solved by the Invention

The ion concentration in a room for ions discharged with the air by the air purifier described in Patent Document 1 corresponds to 1000 to 2000/cm$^3$, which presents a certain level of sterilization effects on bacteria such as serratia, bacillus and the like. The number of ions per 1 cm$^3$ is, however, small for virus, presenting only a small sterilizing effect of decomposing and eliminating virus as well as a small eliminating effect of eliminating odor attached to curtains, clothes and the like. Hence, an ion generating apparatus that can increase the concentration of ions in a room has been desired.

To increase the ion concentration in a room, the number of ions generated by an ion generating section arranged in an air-flowing path for the air blown by an air blower may be increased. However, even if the number of ion generating sections arranged in one air-flowing path is increased, the number of ions will not be multiplied. The number of ions in the air-flowing path will only be saturated, making it difficult to significantly increase the number of ions.

The present invention has been contrived in view of the above circumstances and has a main object of providing an ion generating apparatus that has an increased effect of sterilization of virus and elimination of odor attached to curtains, clothes and the like, and that can increase ion concentration of ions discharged in a room with the air by including a motor having output shafts on both sides in the axial direction and two impellers respectively mounted on the output shafts, and including two air-flowing paths that individually guide the airflow generated by rotation of the respective impellers and discharge the air to the outside, an ion generating section being arranged at each of the air-flowing paths.

With the conventional ion sensor or ion detecting apparatus, however, the degree of insulation of a member that holds an electrode collecting or capturing ions in the air has a great effect on accuracy for detecting ions, which presents a problem in that the degree of insulation of the member decreases when contamination such as dust is attached or when the air in which ions are to be detected has high humidity, resulting in inaccurate detection of ions.

The present invention has been contrived in view of the above circumstances and has an object of providing an ion detecting apparatus and an ion generating apparatus that can detect ions with high accuracy while suppressing adverse effects of humidity or contamination by dust and the like.

Even if a plurality of ion generators are arranged in one air-flowing path, however, the amount of generated ions will not be multiplied since the concentration of ions in the air-flowing path becomes saturated. It is therefore difficult to effectively increase the concentration of ions in a room.

The present invention has been contrived in view of the above circumstances and has an object of providing an ion generating apparatus that can generate highly-concentrated ions by preventing ions generated by a plurality of ion generators from interfering with each other.

Means for Solving the Problems

An ion generating apparatus according to the present invention, comprising an air blower and an ion generating section that generates ions, and configured to discharge the ions generated by the ion generating section to the outside with air blown out by the air blower is characterized in that the air blower includes a motor having output shafts on both sides in a direction of axis and includes two impellers mounted on the respective output shafts, the ion generating apparatus comprises two air-flowing paths that individually let through the air blown out by rotation of each of the impellers to discharge the air to the outside the apparatus, and the ion generating section is arranged in each of the air-flowing paths.

According to the invention, one motor rotates two impellers to discharge the airflow generated by rotation of the impellers from two air-flowing paths to the outside, and an ion generating section is arranged at each of the air-flowing paths, so that the ion concentration of ions discharged in a room with the air can be increased. Therefore, a sterilization effect of decomposing virus and sterilizing can be increased, while infection with virus in a room can be reduced. Moreover, the elimination effect of eliminating odor attached to curtains, clothes and the like can be increased.

The ion generating apparatus according to the present invention is preferably configured such that a part or the whole of the air-flowing path has a laminar flow section where the air flow becomes laminar flow, and the ion generating section is arranged at each laminar flow section.

According to the invention, an ion generating section is arranged at a laminar flow section in which the airflow generated by rotation of each impeller individually becomes laminar flow, allowing the air of laminar flow passing through each air-flowing path to effectively include ions generated by the ion generating section, and increasing ion concentration of ions discharged in a room together with the air. Hence, sterilization effect of decomposing virus and sterilizing can be increased, while infection with virus in the room can be reduced. Moreover, elimination effect of removing odor attached to curtains, clothes and the like can be increased.

Moreover, the ion generating apparatus according to the present invention preferably comprises a rectification body that rectifies the air blown out by rotation of the impeller, the ion generating section being arranged at the rectification body.

According to the invention, ions can effectively be included in the air rectified by the rectification body and passing through as laminar flow, so that the ion concentration of the ions discharged in a room together with the air can be increased, enhancing the sterilizing effect of virus.

In the ion generating apparatus according to the present invention, the rectification body may preferably a casing that houses the impellers.

According to the invention, ions can effectively be included in the air that passes through a comparatively narrow path in the casing as laminar flow, further increasing the ion concentration of ions discharged in a room together with the air.

Moreover, the ion generating apparatus according to the present invention is preferably configured such that the casing has two circular-arc guide walls that guide the air blown out by rotation of the impellers and two blowing ports opened from a part of the circular-arc guide wall toward one direction of a tangent line of each circular-arc guide wall, and the ion generating section is arranged at each of the circular-arc guide walls.

According to the present invention, ions can be included in the air of laminar flow that passes through a comparatively narrow path in the casing at high wind speed, so that the ions generated by the ion generating section can more effectively be included in the air, further increasing ion concentration of ions discharged in a room together with the air.

The ion generating apparatus according to the present invention is preferably configured such that each of the air-flowing paths has a tube section formed such that the upward flow of the air blown out from each blowing port becomes laminar flow, and the ion generating section is arranged at each tube section.

According to the present invention, a laminar flow section is arranged at each of the tube sections continuing into each of the blowing ports and an ion generating section is arranged at each of the tube sections, so that an ion generating section can be provided without the need for increasing the size of the surrounding area of the air blower, allowing the ion generating apparatus to be reduced in size.

The ion generating apparatus according to the present invention is preferably configured such that two wind directing bodies are arranged to be freely removable at a discharging end of each of the air-flowing paths.

According to the present invention, wind direction of the two wind directing bodies are made different, so that the discharging direction of ions can be changed to adapt living conditions in a room, allowing effective discharge of ions in the room.

Moreover, the ion generating apparatus according to the present invention is preferably configured such that each of the wind directing bodies has a wind directing section that changes a discharging direction of the air to a direction diagonal to the discharging direction of the air discharged upward from each of the tube sections.

According to the invention, total amount of ions can be discharged in the same direction by forming the two wind-directing bodies to have the same wind direction, or a half of ions can be discharged in one direction while the remaining half of ions can be discharged in another direction by forming the two wind-directing bodies to have opposite directions. This can prevent ions discharged from the two wind-directing bodies from interfering with each other in a room.

Moreover, the ion generating apparatus according to the present invention is preferably configured such that more than one of the ion generating sections are arranged separately from each other in a direction intersecting with the air-flowing direction in which the air passes through.

According to the invention, the number of portions where ions generated by the ion generating section are included in the air of laminar flow passing through a comparatively narrow air-flowing path may be increased, allowing the ions generated by the ion generating section to more effectively be included in the air. Therefore, ion concentration of ions discharged from the discharge port together with the air can further be increased.

The ion generating apparatus according to the present invention is preferably configured such that more than one of the ion generating sections are arranged separately from each other in the air-flowing direction.

According to the invention, the number of portions where ions are included in the air of laminar flow passing through a comparatively narrow air-flowing path can further be increased, so that the ions generated by the ion generating section can more effectively be included in the air, further increasing the ion concentration of the ions discharged from the discharge port together with the air.

An ion detecting apparatus according to the present invention having a measurement section that measures a potential of a collecting electrode which collects ions in the air and detecting ions based on the potential measured by the measurement section is characterized by comprising a protective electrode that encloses the collecting electrode and is to be connected to a given potential.

According to the invention, the protective electrode which is to be connected to a given potential is configured to enclose the collecting electrode, preventing the charge held by the ions collected by the collecting electrode from being conducted through a portion where insulation is degraded due to contamination such as dust or moisture of the surrounding air and moving to the outside of the area enclosed by the protective electrode.

The ion detecting apparatus according to the present invention is characterized in that the protective electrode has a missing portion of the electrode in a section where the air in which ions are to be detected flows toward the collecting electrode.

According to the invention, a missing portion is provided at a part of the protective electrode, preventing, when the missing portion is directed in the air-flowing direction of the air in which ions are to be detected, the collecting electrode from collecting ions in the air that are not to be detected while preventing the protective electrode from collecting ions that are to be detected. This enhances accuracy of detection of targeted ions.

The ion detecting apparatus according to the present invention is characterized in that the measurement section has a converter that converts impedance of the collecting electrode, and the protective electrode is configured to be connected to an output terminal of the converter and to have a potential approximately the same as the potential of the collecting electrode.

According to the present invention, the protective electrode is connected to the output terminal of the impedance converter of the measurement section to obtain approximately the same potential as the collecting electrode, preventing the charge held by the ions collected by the collecting electrode from being conducted through the inside of the area enclosed by the protective electrode and moving to the protective electrode.

The ion detecting apparatus according to the present invention is characterized in that the measurement section has a circuit element connected between the collecting electrode and the converter, and the protective electrode encloses both ends of the circuit element.

According to the invention, a resistance for protecting a circuit element such as a converter, for example, is provided between the collecting electrode and the converter, and the protective electrode encloses both terminals of the circuit element and the portions connected to the both terminal. This can prevent the converter from being directly applied with high voltage due to static electricity or the like. Moreover, the portion ranging from the collecting electrode to the converter is enclosed by the protective electrode, preventing the charge held by ions collected by the collecting electrode from moving to the outside of the area enclosed by the protective electrode from that portion.

The ion detecting apparatus according to the present invention is characterized in that the measurement section has a resistance that pulls up the collecting electrode to a positive given potential, and is configured to measure the potential of a collecting electrode that collects negative ions.

According to the invention, the collecting electrode is pulled up to a given positive potential by a resistance, so that the potential of the collecting electrode is significantly lowered when the collecting electrode collects negative ions.

This allows detection of negative ions. Hence, for the negative ion generating section where a foreign material such as silicon may easily be attached to the electrode to cause reduction in the amount of generated ions, abnormality in the amount of generated ions can be detected.

The ion detecting apparatus according to the present invention is characterized by comprising a circuit substrate on which the measurement section is arranged on one surface, wherein the collecting electrode is arranged on another surface of the circuit substrate, and the protective electrode is configured to enclose the measurement section.

According to the present invention, the measurement section is arranged on one surface of the circuit substrate whereas the collecting electrode is arranged on another side thereof, and the protective electrode encloses the measurement section. Therefore, the collecting electrode is connected to the measurement section with a minimum distance, preventing unnecessary moving of charges and allowing reduction in size of the entire ion detecting apparatus. Moreover, the charge held by ions collected by the collecting electrode can be prevented from crossing over the circumference of the circuit substrate and moving to the measurement section.

An ion generating apparatus according to the present invention is characterized by comprising the ion detecting apparatus according to the present invention, an ion generator that generates ions, and a means for outputting a warning based on a result of detection of ions performed by the ion detecting apparatus.

According to the invention, a warning is outputted to the user based on the result of detection, for the ions generated by the ion generator, performed by the ion detecting apparatus. This allows the user to be notified of lowering of the amount of generated ions when it is lowered, and to be urged to clean the ion generating section or to change the ion generator.

The ion generating apparatus according to the present invention is characterized in that the collecting electrode is arranged in the vicinity of the ion generator, and that the ion generator has a booster transformer and is directed in a direction in which a probability that a flux leaking from the booster transformer interlinks with the collecting electrode is suppressed.

According to the invention, the collecting electrode is arranged in the vicinity of the ion generator, allowing detection of ions with high sensitivity. Moreover, the ion generator is directed in the direction in which the flux leaking from the booster transformer, which is provided to obtain high voltage for generating ions, minimally interlinks with the collecting electrode, preventing conductive current generated at the collecting electrode from cancelling the flux, so that the high voltage may be stabilized.

The ion generating apparatus according to the present invention is characterized in that the ion detecting apparatus is directed in a direction in which a probability that a flux leaking from the booster transformer interlinks with a portion enclosed by the protective electrode is suppressed.

According to the invention, the ion detecting apparatus is directed in the direction in which the flux leaking from the booster transformer of the ion generator minimally interlinks with the portion enclosed by the protective electrode, preventing conductive current generated at the protective electrode from cancelling the flux, so that the high voltage is stabilized.

As described above, it has conventionally known that $H^+(H_2O)_m$ (m is an arbitrary natural number), which is a positive ion, and $O_2^-(H_2O)_n$ (n is an arbitrary natural number), which is a negative ion, sterilize floating bacteria or the like in the air by reaction of ions. The ions, however, recombine with each other and disappear. Thus, even if high concentration of ions can be realized in the proximity of the ion generator, the concentration thereof is rapidly lowered as the distance from the ion generator becomes farther. Hence, even if the concentration of ions can be several tens of thousands/$cm^3$ in a small-volume space such as an experimental apparatus, only two to three thousand ions/$cm^3$ at the most can be achieved in a large-volume space such as an actual residential space or work space.

The inventors, on the other hand, have found that bird influenza virus can be removed, in an experimental laboratory level, by 99% in ten minutes when the ion concentration of 7,000 ions/$cm^3$ is achieved and by 99.9% when that of 50,000 ions/$cm^3$ is achieved. These numbers of removal rates mean that, if there are 1,000 viruses/$cm^3$ in the air, 10 virus/$cm^3$ and 1 virus/$cm^3$ remain, respectively. In other words, by increasing the ion concentration from 7,000 ions/$cm^3$ to 50,000 ions/$cm^3$, the remaining viruses will be reduced to one tenth. This shows that it is very important for protection against infectious diseases and environmental purification to increase the ion concentration in the entire residential space or work space where a person or the like lives.

An ion generating apparatus according to the present invention is based on the above knowledge, which discharges ions generated by a plurality of ion generators from a discharge port together with suctioned air, and is characterized by comprising more than one of the discharge ports, and a diversion body that divides the air from one or more of the ion generators, different for each discharge port, toward each of the discharge ports.

According to the present invention, the diversion body divides the suctioned air into respective discharge ports from one or more ion generators specific to each discharge port. This can prevent ions generated by the ion generator specific to each discharge port from overlapping and interfering with each other.

The ion generating apparatus according to the present invention is characterized in that a plurality of ion generators for which the diversion body divides and flows the air to one of the discharge ports are configured to be energized in different phases.

According to the invention, a plurality of ion generators that are specific to one discharge port are energized in different phases, which reduces probability that ions generated by the plurality of ion generators interfere with one another.

The ion generating apparatus according to the present invention is characterized in that the plurality of ion generators are configured to be alternately energized.

According to the present invention, a plurality of ion generators that are specific to one discharge port are alternately energized, preventing ions generated by the plurality of ion generators from interfering with each other.

The ion generating apparatus according to the present invention is characterized in that the plurality of ion generators are configured to be energized at an equal duty.

According to the invention, the plurality of ion generators that are specific to one discharge port are energized in an equal duty, multiplying the operational lifetime of each of the plurality of ion generators.

The ion generating apparatus according to the present invention is characterized by comprising two discharge ports, and two sets of ion generators, a set including the ion generators arranged next to each other, wherein the air is divided and flown from one and another of each set of ion generators to one and another of the discharge ports, and each set of ion generators is configured to be alternately energized at an equal duty.

According to the invention, for the adjacent two sets of ion generators, the suctioned air is divided from one and the other of each set to one and the other of the two discharge ports. Moreover, each set of ion generators are alternately energized at an equal duty. This prevents the adjacent ion generators from, for example, electromagnetically interfering with each other, and multiplies the operational lifetime for all the ion generators.

The ion generating apparatus according to the present invention is characterized by comprising: a detection means for detecting an amount of ions; a determination means for determining whether or not the amount of ions detected by the detection means is equal to or lower than a given amount; and a warning means for outputting a warning when the determination means determines that the amount is equal to or lower than the given amount.

According to the present invention, the warning means outputs a warning when the amount of ions detected by the detection means is equal to or lower than a given amount. This can increase reliability and make the apparatus suitable for continuous operation for professional use.

The ion generating apparatus according to the present invention is characterized in that the detection means is configured to detect the amount of ions at a portion where ions are generated, a portion where ions are discharged or a given portion outside.

According to the invention, the detection means can detect the amount of ions at any of the three different portions, so that the portion where the amount of ions is to be detected can flexibly response to different uses and/or purposes.

The ion generating apparatus according to the present invention is characterized by comprising: a means for detecting current flowing in an ion generator; and a means for determining whether or not a current value detected by the means for detecting is equal to or higher than a given value when the ion generator is energized, wherein the warning means outputs a warning when the means for determining determines that the current value is less than the given value.

According to the invention, if it is determined that the current flowing in the ion generator is equal to or lower than a given value when the ion generator is being energized, the warning means outputs a warning.

This can facilitate recognition of normality of the ion generator and can further increase reliability.

Effects of the Invention

According to the present invention, one motor rotates two impellers, while the air generated by the rotation of each impeller is discharged to the outside from two air-flowing paths, in which ion generating sections are respectively arranged, so that ion concentration of ions discharged in a room together with the air can be increased. Hence, the sterilization effect of virus can be increased, reducing the possibility of being infected with virus in a room. Moreover, the elimination effect of eliminating the odor attached to curtains, clothes and the like can be increased.

Furthermore, according to the present invention, an ion generating section is arranged at the laminar flow portion configured to individually let through the airflow generated by rotation of each impeller as laminar flow, so that the ions generated by the ion generating section can effectively be included in the air passing through each air-flowing path, increasing ion concentration of ions discharged in a room together with the air. Hence, the sterilization effect for virus can be increased while the elimination effect of eliminating the odor attached to curtains, clothes or the like can be increased.

According to the invention, the protective electrode encloses the collecting electrode, preventing the charge held by ions collected by the collecting electrode from being conducted through the portion where insulation is lowered due to contamination such as dust or moisture in the surrounding air and moving to the outside of the area enclosed by the protective electrode. Hence, ions can be detected with high accuracy.

According to the present invention, the diversion body divides and flows the suctioned air from the ion generator to the discharge port. This prevents the ions generated by the ion generator specific to each discharge port from overlapping and interfering with each other. Hence, ions with high concentration can be generated.

BRIEF DESCRIPTION OF THE DRAWINGS

FIG. 12 is a graphic chart illustrating the variation amount of an electric potential measured by an ion detecting apparatus before and after discharge with respect to the number of discharges from an ion generator.

FIG. 27 is a table illustrating measurement examples of average ion concentrations in a certain room in the case where two or four of ion generators are used and where polarity and energized time of ion generating sections are changed.

Figure 1:
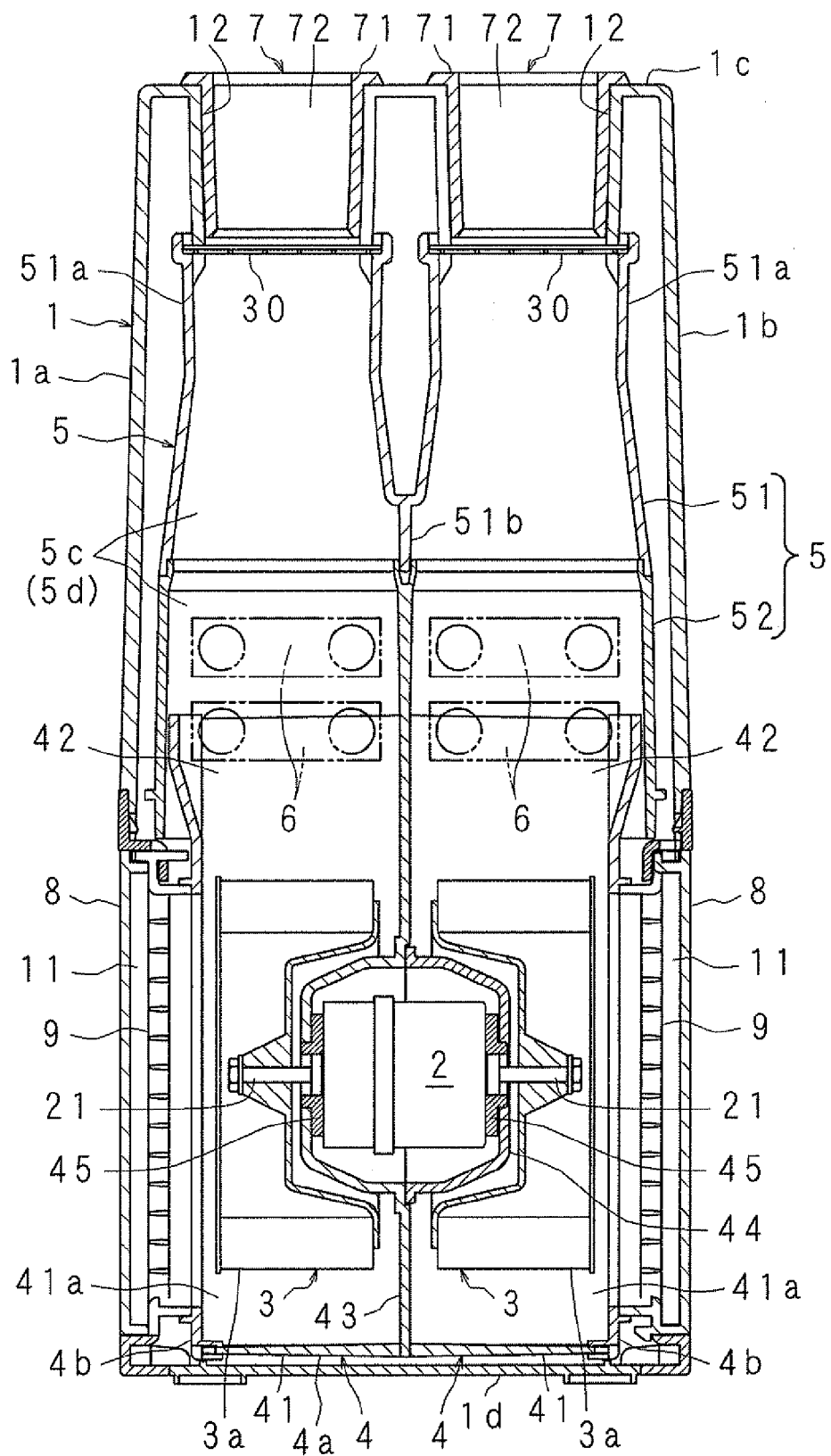
FIG. 1 is a vertical section front view illustrating the configuration of an ion generating apparatus according to the present invention.

DESCRIPTION OF REFERENCE CODES 2 motor
21 output axis
3 impeller (air blower)
4 casing (rectification body)
41 circular-arc guide wall
42 blowing port
5 duct (air-flowing path, tube section)
6 ion generator
61, 62 ion generating section
7 wind directing body
72 wind directing board
F laminar flow section
1 housing
2 motor
3 impeller
4 casing 5 duct
51*a* rectangular tube section
51*b* joint section
6*a*, 6*b*, 6*c*, 6*d* ion generator
61, 62 ion generating section
65 booster transformer (booster voltage inverter)
66 collecting electrode
67 measurement section
69 protective electrode
86 display section (means for outputting a warning)
IC1 operating amplifier (converter)
R1 protective resistance (circuit element)
R4 resistance (pull-up resistance)
K missing portion
1 housing
2 motor
3 impeller
4 casing
41 circular-arc guide wall
43 joint wall (diversion body)
5 duct
51*a* rectangular tube section (part of which being diversion body)
51*b* joint section (diversion body)
6*a*, 6*b*, 6*c*, 6*d* ion generator
61, 62 ion generating section
64 ion sensor (detecting means)
65 ion detecting circuit (detecting means)
12 engagement hole (discharge port)
86 display section (warning means)
92 driving current detecting circuit (means for detecting current)
R1 resistance (means for detecting current)

BEST MODE FOR CARRYING OUT THE INVENTION

Embodiment 1

Figure 2:
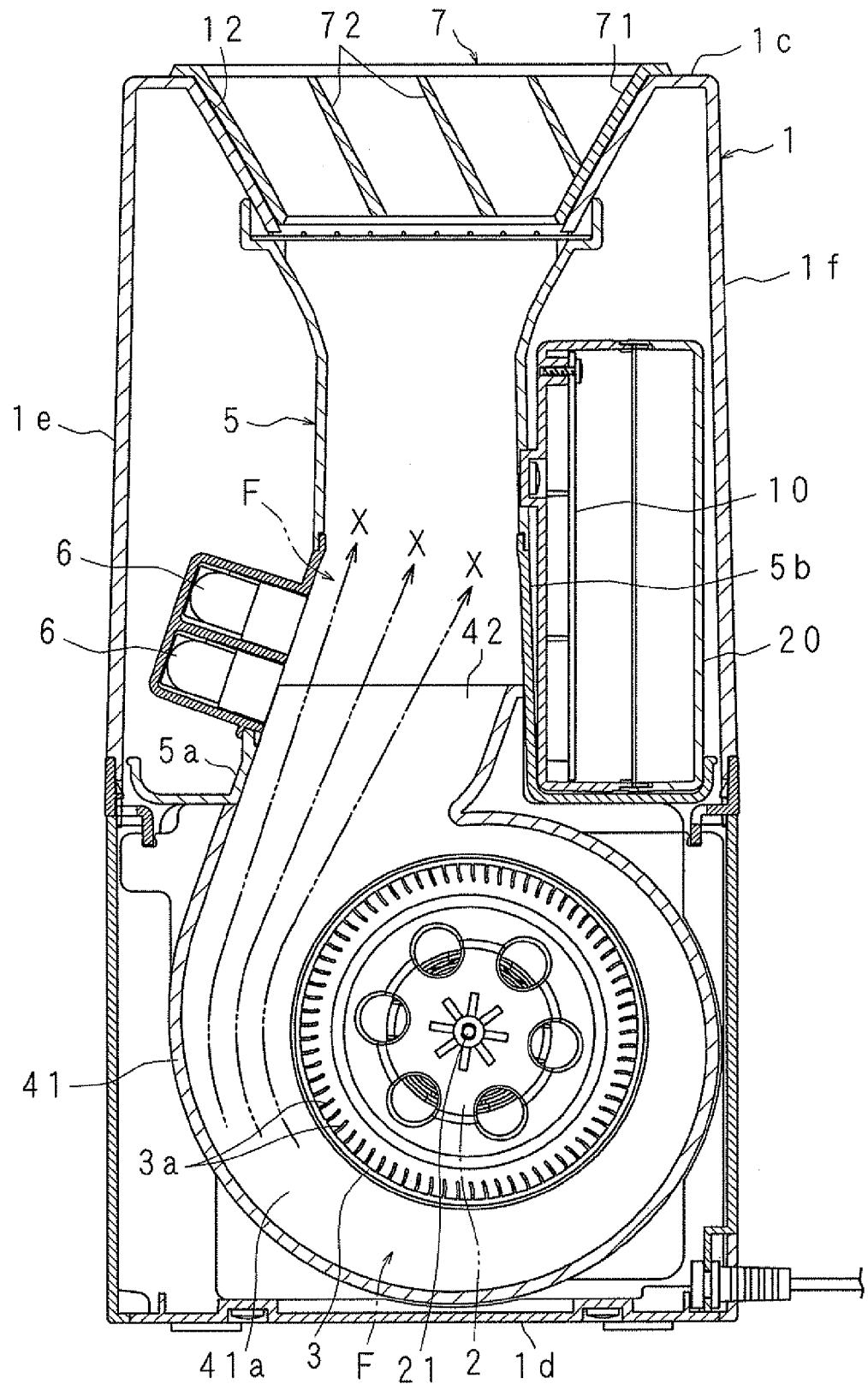
FIG. 2 is a vertical section side view illustrating the configuration of an ion generating apparatus according to the present invention.
Figure 3:
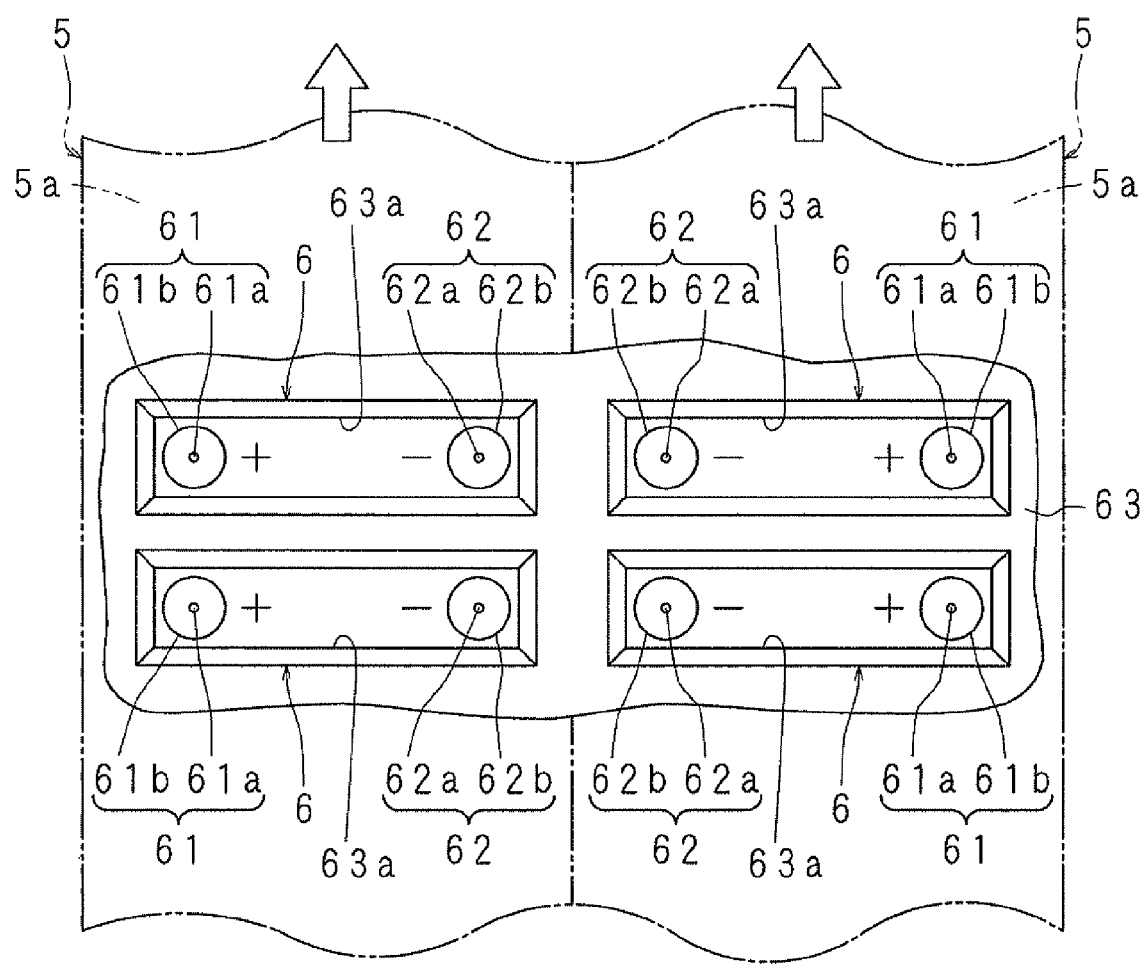
FIG. 3 is a front view illustrating the configuration of an ion generator of an ion generating apparatus according to the present invention, a part of which is not shown.

FIG. 1 is a vertical section front view illustrating the configuration of an ion generating apparatus according to the present invention. FIG. 2 is a vertical section side view illustrating the configuration of the ion generating apparatus. FIG. 3 is a front view illustrating the configuration of the ion generator, a part of which is not shown.

The ion generating apparatus illustrated in FIG. 1 includes: a housing 1 having suction ports 11, 11 at a lower portion of both side walls 1*a*, 1*b* separated and arranged in opposed position and having two engagement holes 12, 12 at a central portion of a top wall 1*c*; a motor 2 arranged at a lower portion in the housing 1 and having output shafts 21, 21 on both sides in the direction of the output shafts; two impellers 3, 3 mounted on the output shafts 21, 21 of the motor 2; two casings 4, 4 that house the impellers 3, 3 such that the impellers 3, 3 are rotatable; two ducts 5, 5 serving as tube sections that leads upward the airflow generated by rotation of the respective impellers 3, 3; ion generators 6, 6 having two ion generating sections 61, 62 and arranged in the middle part of the ducts 5, 5, respectively; and wind directing bodies 7, 7 arranged at the engagement holes 12, 12 in a removable fashion. Note that the motor 2, impellers 3, 3 and casings 4, 4 constitute an air blower.

The housing 1 forms an approximately rectangular parallelepiped shape having a bottom wall 1*d* of a planar rectangle, a front wall 1*e* and a back wall if continuing into two sides of the bottom wall 1*d*, side walls 1*a*, 1*b* continuing into the other two sides of the bottom wall 1*d*, and a top wall 1*c*. Attached to the suction ports 11, 11 at the lower portions of the both side walls 1*a*, 1*b* are filters 8, 8 that pass the air taken in from the suction ports 11, 11 by the impellers 3, 3 and eliminate foreign materials in the air to produce clean air. The engagement holes 12, 12 at the top wall 1*c* has a rectangular shape with its longer directions forming front and back, the inner face of the front side being tilted forward relative to the vertical direction while the inner face of the back side being tilted backward relative to the vertical direction. Moreover, the housing 1 is divided into an upper part and a lower part at the middle thereof in the up-down direction, the lower part being provided with the casings 4, 4 and the upper part being provided with the ducts 5, 5.

The impellers 3, 3 are multi-blade impellers having a plurality of blades 3*a* with the side of its rotating center displaced in the rotating direction relative to the outer edge. In other words, they are Sirocco impellers (Sirocco fans) having a circular cylinder shape. One end of each of the impellers 3, 3 has a bearing board. Each of the output shafts 21, 21 of the motor 2 is placed at a shaft hole opened at the center of the bearing board, which functions such that the air taken in from an opening at the other end to an air hole at the center is released from between the blades 3*a* on the outer circumference.

The casings 4, 4 has circular-arc guide walls 41, 41 that guide the airflow generated by rotation of the impellers 3, 3 in the rotating direction to increase the speed of the airflow, and blowing ports 42, 42 opened upward from a part of the circular-arc guide walls 41, 41 to one direction of tangent lines of the circular-arc guide walls 41, 41. Each of the blowing ports 42, 42 forms a square-tubular shape that protrudes from a part of the circular-arc guide walls 41, 41 in the direction of tangent lines of the circular-arc guide walls 41, 41 and in the direction diagonal to the vertical direction. Moreover, the casings 4, 4 form the shape of deep dishes, including casing bodies 4*a*, 4*a* having the circular arc guide walls 41, 41 and openings for blowing ports 42, 42, and including cover plates 4*b*, 4*b* in which portions corresponding to the openings of the impellers 3, 3 are opened and which close the open side of the casing bodies 4*a*, 4*a*. In the casings 4, 4, the opposing sides of the casing bodies 4*a*, 4*a* are connected together by a joint wall 43 for partitioning. Furthermore, ventilation plates 9, 9 having a plurality of ventilation holes are provided between the open portions of the cover plates 4*b*, 4*b* and filters 8, 8. Note that the air-flowing paths 41*a*, 41*a* provided between the perimeter surfaces of the impellers 3, 3 and the circular-arc guide walls 41, 41 and the front wall 5*a* form a laminar flow portion F.

The portion corresponding to the motor 2 at the joint wall 43 has a concave which is dent toward the side of one casing body 4*a*, while a support plate 44 of a deep-dish shape is attached to the edge of the concave. Rubber plates 45, 45 are placed between the concave and the central part of the support plate 44 to hold the motor 2 in a sandwiched manner. Each of the output shafts 21, 21 is inserted through the shaft hole opened at the concave and the central part of the support plate 44, the impellers 3, 3 being attached to the output shafts 21, 21. Moreover, the upper end of the joint wall 43 is extended to above the casings 4, 4.

The ducts 5, 5 are formed of a tube section having a square-tubular shape, the lower ends thereof continuing into the blowing ports 42, 42, the upper ends thereof continuing into the engagement holes 12, 12, and the middle part thereof in the up-down direction being narrowed down. Moreover, the ducts 5, 5 have: front walls 5*a*, 5*a* extending from the blowing ports 42, 42 along one direction of the tangent lines of the circular-arc guide walls 41, 41; back walls 5*b*, 5*b* arranged approximately vertical from the blowing ports 42, 42; and two sets of approximately-vertically-arranged side walls 5c, 5c, 5d, 5d continuing from the front walls 5a, 5a and back walls 5b, 5b. The ducts 5, 5 are configured to form laminar flow portions F, F on the sides facing the impellers 3, and to let through the air flow blown from the blowing ports 42, 42, as laminar flow, vertically along the front walls 5a, 5a and side walls 5c, 5c, 5d, 5d.

At the front walls 5a, 5a, penetration holes corresponding to the ion generating sections 61, 62 are opened, while the ion generators 6, 6 are engaged to be attached to the penetration holes. At the back walls 5b, 5b, a circuit substrate 10 connected to the motor 2, ion generators 6, 6 and a power line, as well as a cover 20 covering the circuit substrate 10 are mounted. Moreover, the ducts 5, 5 are divided into a duct upper body 51 and a duct lower body 52 at the middle part thereof in the up-down direction. The duct lower body 52 forms a square tubular shape and partitioned at the center thereof in the horizontal direction by the joint wall 43. For the duct upper body 51, the lower part of the square tube sections 51a, 51a separately arranged in parallel with each other in the horizontal direction forms one continuing portion at the joint section 51b, and is partitioned by the joint section 51b and the joint wall 43. Moreover, at the upper end of the duct upper body 51, protection nets 30, 30 are arranged for preventing foreign materials such as a finger from being inserted from the outside.

The ion generators 6, 6 include: two ion generating sections 61, 62 separated in the direction intersecting with the flowing direction of air generated by rotation of the impellers 3, 3; a power feeding section that supplies power voltage to the ion generating sections 61, 62; and a holder 63 that holds the ion generating sections 61, 62 and the power feeding section. The ion generators 6, 6 are configured to supply voltage to the ion generating sections 61, 62 so that the ion generating sections 61, 62 cause corona discharge to generate ions.

The ion generators 61, 62 has discharge electrode convex portions 61a, 62a of peaked shapes and guide electrode rings 61b, 62b enclosing the discharge electrode convex portions 61a, 62a, which are arranged at the central parts of the guide electrode rings 61b, 62b, respectively. The ion generators 6, 6 are configured such that one ion generating section 61 generates positive ions while the other ion generating section 62 generates negative ions.

For the ion generators 6, 6, two are held in one holder 63. Two ion generators 6, 6 are attached on the front walls 5a, 5a of the ducts 5, 5, respectively, and separately arranged in parallel with each other in the air-flowing direction. Moreover, the ion generating sections 61, 62 of two ion generators 6, 6 are arranged side by side at positions intersecting with the air-flowing direction, the adjacent sides having the same polarity. The ion generating sections 61, 62 of the respective ion generators 6, 6 face to the ducts 5, 5 from the penetration holes. Moreover, four parts corresponding to the ion generating sections 61, 62 are opened at the side of the holder 63 where it is attached to the ducts 5, 5. The ion generating sections 61, 62 are arranged at respective openings 63a.

The wind directing bodies 7, 7 have square frame portions 71, 71 with an inverse-trapezoid cross-sectional shape in the front-back direction, and a plurality of wind directing boards 72, 72 that are separately arranged in parallel with each other in the front-back direction in the square frame portions 71, 71 and tilted toward one front-back direction relative to the vertical direction, and are formed in the same shape. The front and back walls of the square frame portions 71, 71 are tilted in the front-back direction relative to the vertical direction.

The ion generating apparatus configured as described above is placed in a residential room. The motor 2 of the air blower is driven to rotate the impellers 3, 3, so that the air in the room is suctioned from the suction ports 11, 11 on both sides into the two casings 4, 4, eliminating foreign materials such as dust in the suctioned air by the filters 8, 8. Here, the air suctioned into the casings 4, 4 becomes airflow passing through along the circular-arc guide walls 41, 41 around the impellers 3, 3 while being rectified by the circular-arc guide walls 41, 41. The rectified air becomes laminar flow at the laminar flow portion F of the air-flowing paths 41a, 41a. This laminar air flow passes through toward the blowing ports 42, 42 along the circular-arc guide walls 41, 41 as indicated by the arrows X of dashed double-dotted lines in FIG. 2, and is blown out from the blowing ports 42, 42 into the ducts 5, 5.

The laminar flow portions F, F exist, viewed from the side, in the air-flowing paths 41a, 41a on the side where the front walls 5a, 5a of the ducts 5, 5 and the circular-arc guide walls 41, 41 are facing the impeller 3. The laminar flow of the air indicated by the arrows X in FIG. 2 passes through the laminar flow portions F, F surrounded by the front walls 5a, 5a, side walls 5c, 5c and side walls 5d, 5d. The ion generators 6, 6 are arranged on the front walls 5a, 5a where the air passes through in such a manner of laminar flow. As described above, the positive and negative ions generated by the ion generating sections 61, 62 of the ion generators 6, 6 may efficiently be included in the air passing through a comparatively narrow passage along the front walls 5a, 5a in the manner of laminar flow. Moreover, the ducts 5, 5 are narrowed down at the middle part thereof in the up-down direction so as to allow passage of the air at high wind speed, allowing the air to efficiently include positive and negative ions. Furthermore, a plurality of ion generators 6, 6 are provided separately from each other in the air-flowing direction so as to increase the number of portions where the air may include ions, allowing the air to efficiently include ions. Note that, in the present embodiment, an example was described where the ion generators 6, 6 are arranged on the front walls 5a, 5a which are at ends of the circular-arc guide walls 41, 41 while facing the blowing ports 42, 42. It is, however, not limited thereto. The ion generators 6, 6 may be provided at other areas as long as they face the laminar flow portions F, F where the laminar flow of the air indicated by the arrows X inside the ducts 5, 5 passes through. For example, the ion generators 6, 6 may also be arranged, when viewed from the side, on a straight line extending from the portion of the circle where the curvature of the circular-arc guide walls 41, 41 is constant to the portion where the curvature gradually decreases upward or the portion where the curvature is infinite.

In fact, when the amount of ions per 1 $cm^3$ of the air discharged in a room was measured with the configuration where two ion generators 6, 6 are arranged on the front walls 5a, 5a of the ducts 5, 5 separately from each other in the air flowing direction, ion concentration of approximately 7000/$cm^3$ was obtained as a result. Thus, the sterilization effect for virus in the room and elimination effect for odor attached to curtains, clothes and the like can be enhanced.

Conventionally, sterilization of floating bacteria by emitting a positive ion $H^+(H_2O)_m$ (m is an arbitrary integer) and a negative ion $O_2^-(H_2O)_n$ (n is an arbitrary integer) to react the ions has been known. The ions, however, recombine with each other and disappear, causing its concentration to be drastically reduced as the distance of emitting becomes longer, even if the high concentration can be achieved in proximity to an ion generating element. Hence, even if the ion concentration of several tens of thousands of ions/$cm^3$ can be achieved in a lower-capacity space such as an experiment system, concentration of only two to three thousand ions/cm$^3$ may be achieved in a larger space such as an actual residential space or work space.

The inventors, on the other hand, have found that, in an experimental laboratory, 99% of bird influenza virus can be eliminated in ten minutes when the concentration of 7,000/cm$^3$ is achieved, while 99.9% of the virus can be eliminated with the ion concentration of 50,000/cm$^3$. The elimination rates mean that, if 1000 viruses exist in the air, 10/cm$^3$ and 1/cm$^3$ remain, respectively. That is, by increasing the ion concentration from 7,000/cm$^3$ to 50,000/cm$^3$, the remaining virus is reduced to one tenth.

Accordingly, in a residential space for people to live or a work space, it is very important for prevention of infectious diseases or environmental purification to not only emit highly concentrated ions but also achieve high concentration of ions in the entire space.

In the embodiment described above, the laminar flow portions F, F where the air flow sent out by rotation of the respective impellers 3, 3 becomes laminar flow are included in the ducts 5, 5, while the ion generating sections 61, 62 are arranged at the laminar flow portions F, F in the ducts 5, 5. Alternatively, the ion generating sections 61, 62 may also be arranged at the circular-arc guide wall having the laminar flow portions F, F where the air flow sent out by rotation of the respective impellers 3, 3 becomes laminar flow. Placement of ion generating sections is not specifically limited.

Moreover, in the embodiment described above, the two ion generators 6, 6 arranged in parallel with and separately from each other in the air-flowing direction at a position where the generators 6, 6 intersect with the air-flowing direction in the two ducts 5, 5. The ion generators 6, 6 in the two air-flowing paths, however, may alternatively be arranged separately from each other in the air-flowing direction.

Embodiment 2

Figure 4:
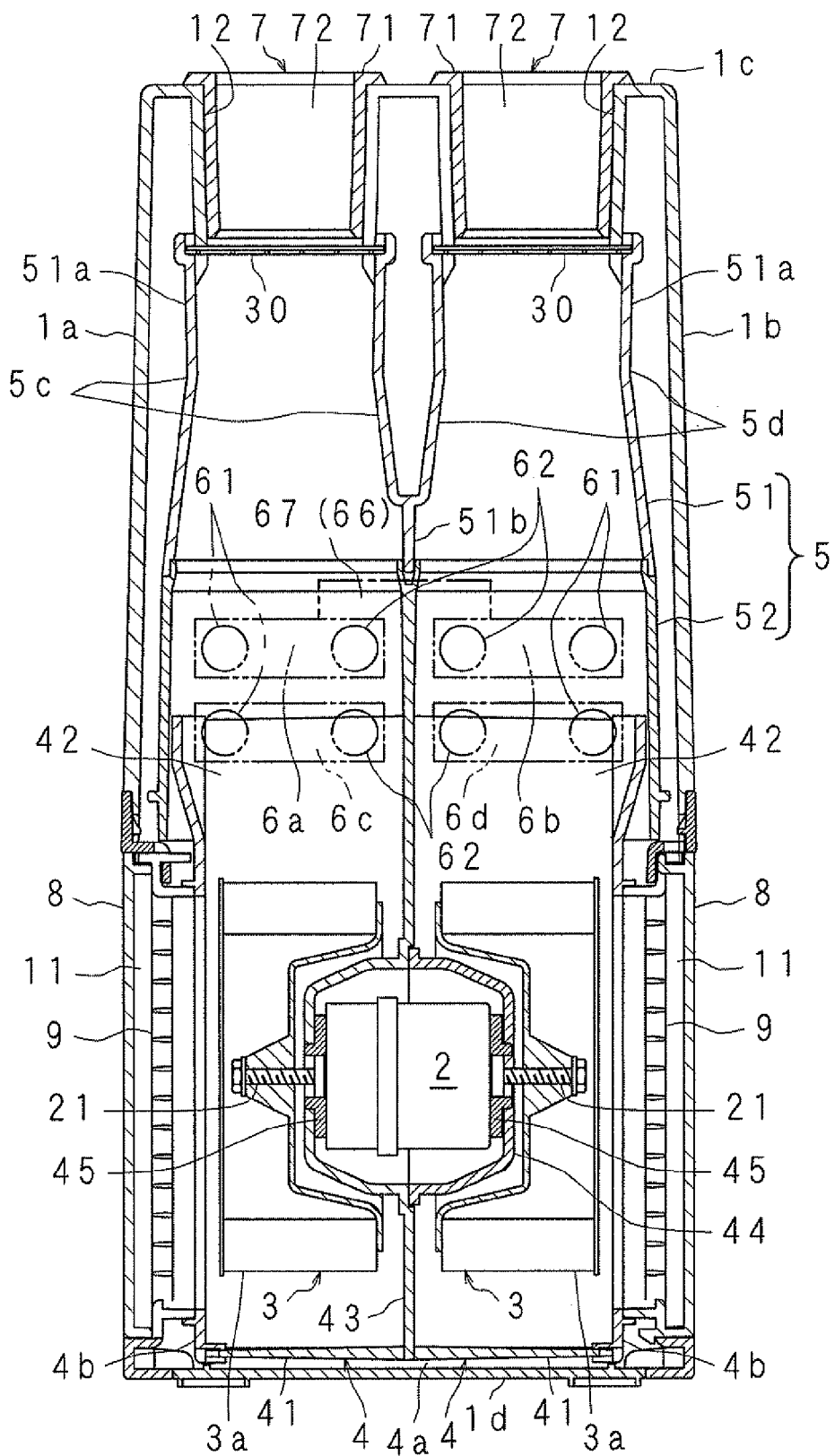
FIG. 4 is a vertical section front view illustrating the configuration of an ion generator according to the present invention.
Figure 5:
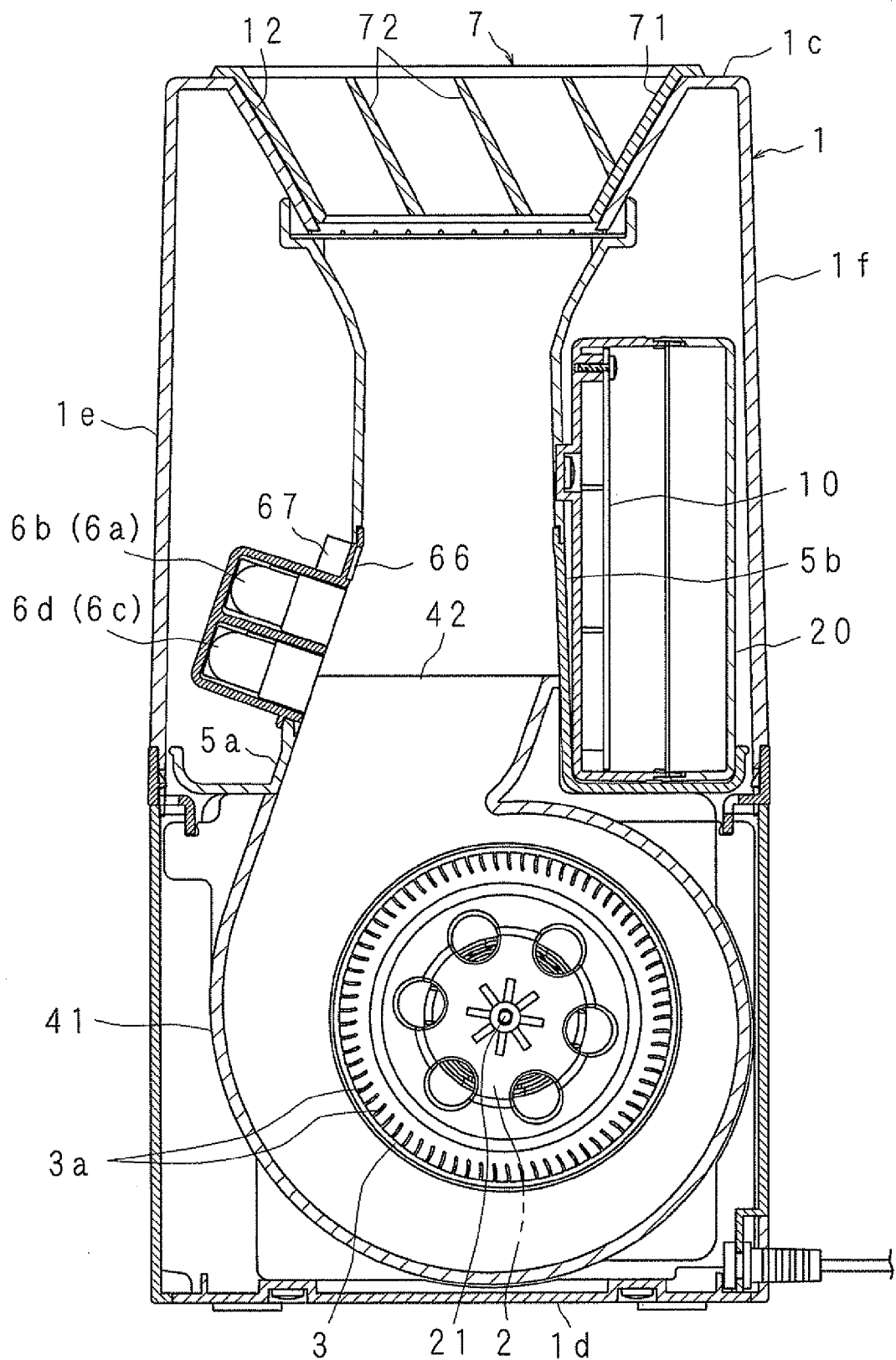
FIG. 5 is a vertical section side view illustrating the configuration of an ion generating apparatus.
Figure 6:
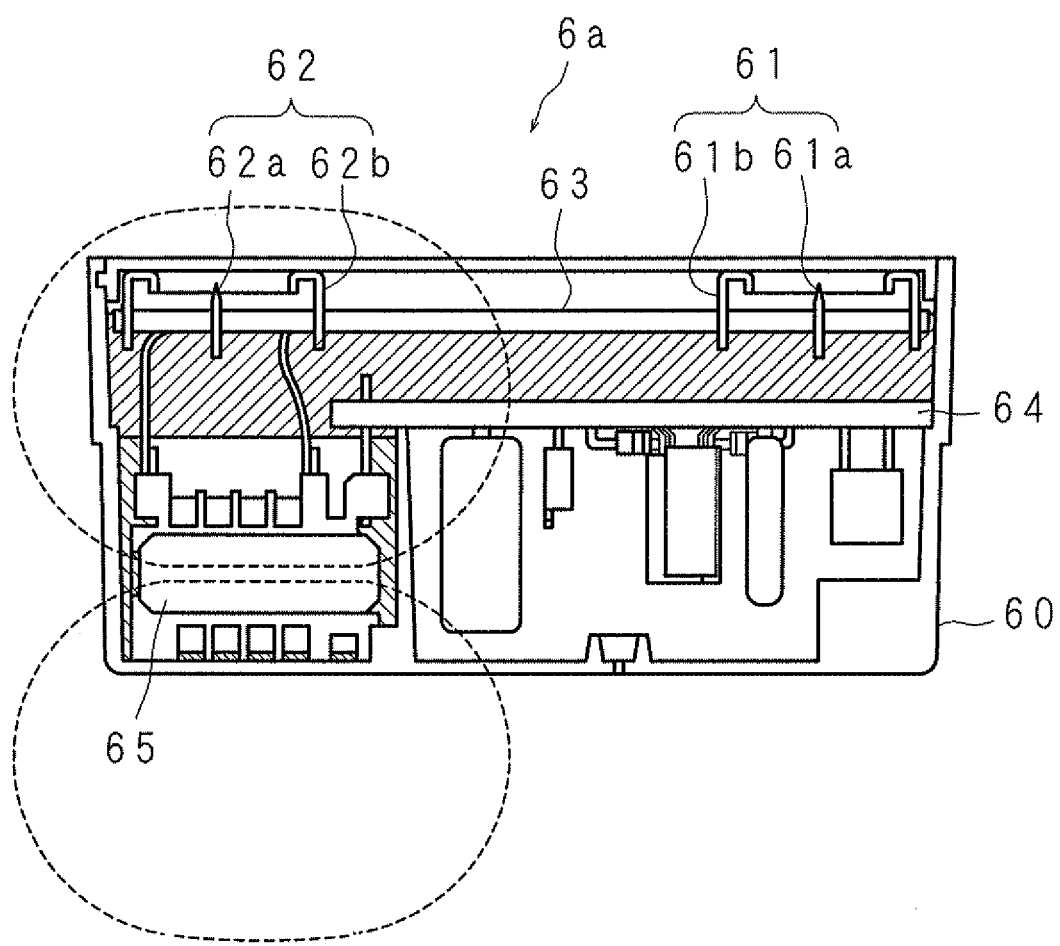
FIG. 6 is a vertical section side view illustrating the configuration of an ion generator.

An embodiment in which the ion detecting apparatus according to the present invention is applied to an ion generating apparatus will be described below in detail. FIG. 4 is a vertical section front view illustrating the configuration of an ion generating apparatus according to the present invention, while FIG. 5 is a vertical section side view illustrating the configuration of an ion generating apparatus. FIG. 6 is a vertical section side view illustrating the configuration of the ion generator 6a. The other ion generators 6b, 6c and 6d have similar configuration as that of the ion generator 6a.

A housing is denoted by 1 in the drawings, the housing 1 including opposing both side walls 1a, 1b having suction ports 11, 11 at lower parts thereof and separated from each other, and a top wall 1c having two engagement holes 12, 12 at the central part thereof. A motor 2 having output shafts 21, 21 on both sides in the direction of rotation axis is provided at the lower part in the housing 1, the output shafts 21, 21 of the motor 2 being provided with two impellers 3, 3 that are housed in two casings 4, 4 to be freely rotatable.

Above the impellers 3, 3, two ducts 5, 5 are respectively arranged as tube sections that individually flow upward the air generated by rotation of the respective impellers 3, 3. The ducts 5, 5 include ion generators 6a, 6c and 6b, 6d, respectively, each having two ion generating sections 61, 62 and include wind directing bodies 7, 7 arranged to be removable at engagement holes 12, 12. Above the ion generators 6a and 6b, a collecting electrode 66 that collects the generated ions and a measurement section 67 that measures the potential of the collecting electrode 66 are so arranged to be adjacent to the ion generators 6a, 6b with their longitudinal direction in parallel with the juxtaposed arrangement direction of the ion generators 6a, 6b. Note that the motor 2, impellers 3, 3 and casings 4, 4 constitute an air blower.

The housing 1 further includes a bottom wall 1d forming a planar rectangle, and a front wall 1e and a back wall 1f continuing into two sides, front and back, of the bottom wall 1d. To the suction ports 11, 11 provided at the lower part of the both side walls 1a, 1b, filters 8, 8 are attached that allow passage of the air suctioned by the impellers 3, 3 from the suction ports 11, 11 to eliminate foreign materials in the air to purify the air. Each of the engagement holes 12, 12 at the top wall 1c forms a rectangle with its longitudinal direction being front and back. The inner surface of the engagement hole 12 on the front side is tilted forward relative to the vertical direction, while the inner surface thereof on the back side is tilted backward relative to the vertical direction. Moreover, the housing 1 is divided into an upper body and a lower body in the middle part thereof in the up-down direction, casings 4, 4 being mounted at the lower body while ducts 5, 5 being mounted at the upper body.

The impellers 3, 3 are multi-blade impellers having a plurality of blades 3a with the side of its rotating center displaced in the rotating direction relative to the outer edge. In other words, they are Sirocco impellers (Sirocco fans) having a circular cylinder shape. One end of the impellers 3, 3 has a bearing board, output shafts 21, 21 of the motor 2 being placed at a shaft hole opened at the center of the bearing board, which functions that the air taken in from an opening at the other end to an air hole at the center is released from between the blades 3a on the outer circumference.

The casings 4, 4 has circular-arc guide walls 41, 41 that guide the airflow generated by rotation of the impellers 3, 3 in the rotating direction to increase the speed of the airflow, and blowing ports 42, 42 opened upward from a part of the circular-arc guide walls 41, 41 to one direction of the tangent lines of the circular-arc guide walls 41, 41. Each of the blowing ports 42, 42 forms a square-tubular shape that protrudes from a part of the circular-arc guide walls 41, 41 to one direction of the tangent lines of the circular-arc guide walls 41, 41 and in the direction diagonal to the vertical direction.

Moreover, the casings 4, 4 form the shape of deep dishes, including casing bodies 4a, 4a having the circular arc guide walls 41, 41 and openings for blowing ports 42, 42, including cover plates 4b, 4b in which portions corresponding to the openings of the impellers 3, 3 are opened and which close the open side of the casing bodies 4a, 4a. The opposing sides of the casing bodies 4a, 4a are connected together by a joint wall 43 for partitioning. Furthermore, ventilation plates 9, 9 having a plurality of ventilation holes are provided between the open portions of the cover plates 4b, 4b and the filters 8, 8.

The portion corresponding to the motor 2 at the joint wall 43 has a concave which is dent toward the side of one casing body 4a, while a support plate 44 of a deep-dish shape is attached to the edge of the concave. Rubber plates 45, 45 are placed between the concave and the central part of the support plate 44 to hold the motor 2 in a sandwiched manner. Each of the output shafts 21, 21 is inserted through the shaft hole opened at the concave and the central part the support plate 44, the impellers 3, 3 being attached to the output shafts 21, 21. Moreover, the upper end of the joint wall 43 is extended to above the casings 4, 4.

The ducts 5, 5 are formed of a tube section having a square-tubular shape, the lower ends thereof continuing into the blowing ports 42, 42, the upper ends thereof continuing into the engagement holes 12, 12, and the middle part thereof in the up-down direction being narrowed down. Moreover, the ducts 5, 5 have front walls 5a, 5a arranged along the line extending from the blowing ports 42, 42 to one direction of the tangent lines of the circular-arc guide walls 41, 41, and back walls 5b, 5b arranged approximately vertical from the blowing ports 42, 42. Two sets of approximately-vertically-arranged side walls 5c, 5c, 5d, 5d continue from the front walls 5a, 5a and back walls 5b, 5b. The ducts 5, 5 are configured to generate laminar flow from the air blown out from the blowing ports 42, 42 along the front walls 5a, 5a and side walls 5c, 5c, 5d, 5d such that the laminar flow vertically passes through.

At the front walls 5a, 5a, penetration holes corresponding to the ion generating sections 61, 62 are opened, and the ion generators 6a, 6b, 6c, 6d are engaged to be attached to the penetration holes. At the back walls 5b, 5b, a circuit substrate 10 connected to the motor 2, ion generators 6a, 6b, 6c, 6d, the measurement section 67 and a power line, as well as a cover 20 covering the circuit substrate 10 are mounted.

Moreover, the ducts 5, 5 are divided into a duct upper body 51 and a duct lower body 52 at the middle part thereof in the up-down direction. The duct lower body 52 forms a square tubular shape and partitioned at the center thereof in the horizontal direction by the joint wall 43. For the duct upper body 51, the lower part of the square tube sections 51a, 51a separately arranged in parallel with each other in the horizontal direction forms one continuing portion at the joint section 51b, and is partitioned by the joint section 51b and the joint wall 43. Moreover, at the upper end of the duct upper body 51, protection nets 30, 30 are arranged for preventing foreign materials such as a finger from being inserted from the outside.

The wind directing bodies 7, 7 have square frame portions 71, 71 with an inverse-trapezoid cross-sectional shape in the front-back direction, and a plurality of wind directing boards 72, 72 that are separately arranged in parallel with each other in the front-back direction within the square frame portions 71, 71 and tilted toward one side in the front-back direction relative to the vertical direction, and are formed in the same shape. The front and back walls of the square frame portions 71, 71 are tilted in the front and back directions relative to the vertical direction.

Each of the ion generators 6a, 6b, 6c, 6d is housed in a case 60 of an approximately-rectangular-parallelepiped shape, including two ion generating sections 61, 62 separated from each other in the direction approximately perpendicular to the air-flowing direction of the air generated by rotation of the impellers 3, 3. The ion generators 61, 62 are arranged on an electrode substrate 63, having discharge electrodes 61a, 62a forming a peaked shape and induction electrodes 61b, 62b enclosing the discharge electrodes 61a, 62a. The discharge electrodes 61a, 62a generate corona discharge when high voltage is applied thereto. This configuration causes one ion generating section 61 to generate positive ions while causing the other ion generating section 62 to generate negative ions.

At the side opposite from the electrode substrate 63, a circuit substrate 64 is provided on which circuit elements such as a transistor and a resistance are arranged, the circuit substrate 64 having a booster transformer (booster inverter) 65 generating the high voltage at the side opposite from the negative ion generating section 62. The winding direction of a winding wire of the booster transformer 65 is determined such that the flux leaking from the winding wire becomes approximately parallel with the juxtaposed direction of the ion generating sections 61, 62 near the ion generating section 62 (indicated by the dashed line in FIG. 6). Synthetic resin is filled between the electrode substrate 63 and the circuit substrate 64, and around the booster transformer 65.

A set of the ion generators 6a, 6b and a set of the ion generators 6c, 6d are arranged such that the negative ion generating sections 62 are facing each other and the generators in each set are next to each other in the direction approximately perpendicular to the air-flowing direction. The sets are separated from and jaxtaposed to each other in the air-flowing direction. The ion generating sections 61, 62 of each ion generators 6a, 6b, 6c, 6d are facing to the duct 5, 5 from the penetration holes.

The collecting electrode 66 is formed of a plate-like electrode having an approximately rectangular shape that collects ions, the electrode surface thereof being arranged in proximity to the ion generating sections 62, 62 and exposed into the ducts 5, 5 so as to detect particularly negative ions generated by the ion generating sections 62, 62 of the respective ion generators 6a, 6b. The electrode surface of the collecting electrode 66 is so arranged to be approximately parallel with the direction in which the ion generators 6a, 6b are positioned side by side (that is, the juxtaposing direction of the ion generating sections 61, 62). This allows the flux leaking from the booster transformers 65, 65 to be approximately parallel with the electrode surface of the collecting electrode 66 at a portion opposite from the ion generating sections 62, 62, so that the flux minimally interlinks with the collecting electrode 66.

The ion generating apparatus configured as described above is installed in a residential room. The motor 2 of the air blower is driven to rotate the impellers 3, 3, by which the air in the room is suctioned from the suction ports 11, 11 on both sides into two casings 4, 4, eliminating foreign materials such as dust in the suctioned air by the filters 8, 8. Here, the air suctioned into the casings 4, 4 forms laminar flow by the circular-arc guide walls 41, 41 around the impellers 3, 3, the laminar airflow passing through along the circular-arc guide walls 41, 41 toward the blowing ports 42, 42 which blow the air into the ducts 5, 5.

Figure 7:
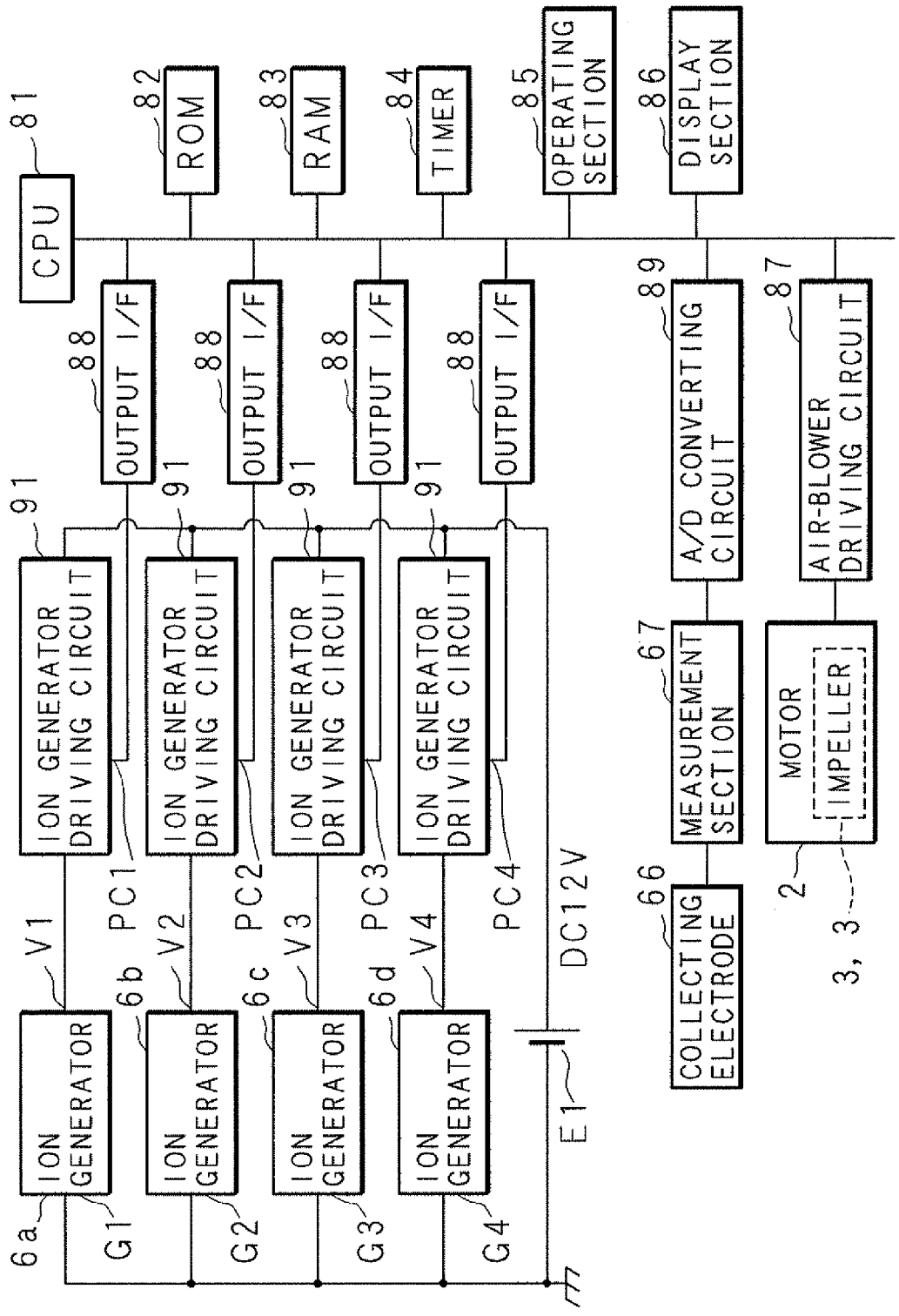
FIG. 7 is a block diagram illustrating schematic configuration of a control system in an ion detecting apparatus and an ion generating apparatus.

FIG. 7 is a block diagram illustrating schematic configuration of a control system in an ion detecting apparatus and an ion generating apparatus. Serving as the center of the control system is a CPU 81, which is connected by bus interconnection with a ROM 82 storing information such as a program and the like, a RAM 83 storing temporarily-generated information and a timer 84 for keeping time. The CPU 81 executes processing such as input/output, calculation and the like in accordance with the control program stored in the ROM 82 in advance.

Further connected by bus interconnection with the CPU 81 are: an operating section 85 for receiving operation to change the air volume of the ion generating apparatus; a display section (means for outputting a warning) 86 constituted by an LED which displays information such as a warning, an operating condition and the like; an air-blower driving circuit 87 for driving the motor 2 on which the impellers 3, 3 are mounted; and an A/D converting circuit 89 for converting an analog voltage measured by the measurement section 67 that measures the potential of the collecting electrode 66 into a digital voltage to take in the voltage. Note that the collecting electrode 66, the measurement section 67, the A/D converting circuit 89, the CPU 81, the ROM 82, the RAM 83 and the timer 84 constitute the ion detecting apparatus.

The output sides of the output interfaces 88, 88, 88, 88 connected by bus interconnection with the CPU 81 are connected to control inputs PC1, PC2, PC3, PC4 of the ion generator driving circuits 91, 91, 91, 91, respectively. One ends of the respective outputs of the ion generator driving circuits 91, 91, 91, 91 are connected to the positive electrode of a 12V direct-current power supply E1, the negative electrode of which is connected to ground inputs G1, G2, G3 and G4 of the respective ion generators 6a, 6b, 6c, 6d and to the ground potential. The other ends are connected to the power inputs V1, V2, V3 and V4 of the ion generators 6a, 6b, 6c and 6d.

In the configuration as described above, every time the timer 84 times a given time, the CPU 81 inverts on/off of the control inputs PC1, PC2, PC3 and PC4 of the ion generator driving circuits 91, 91, 91, 91 via the output interfaces 88, 88, 88, 88. This makes the ion generator driving circuits 91, 91, 91, 91 connect/disconnect the connection between the power inputs V1, V2, V3, V4 of the respective ion generators 6a, 6b, 6c, 6d and the positive electrode of the direct-current power supply E1 at every given time.

Figure 8:
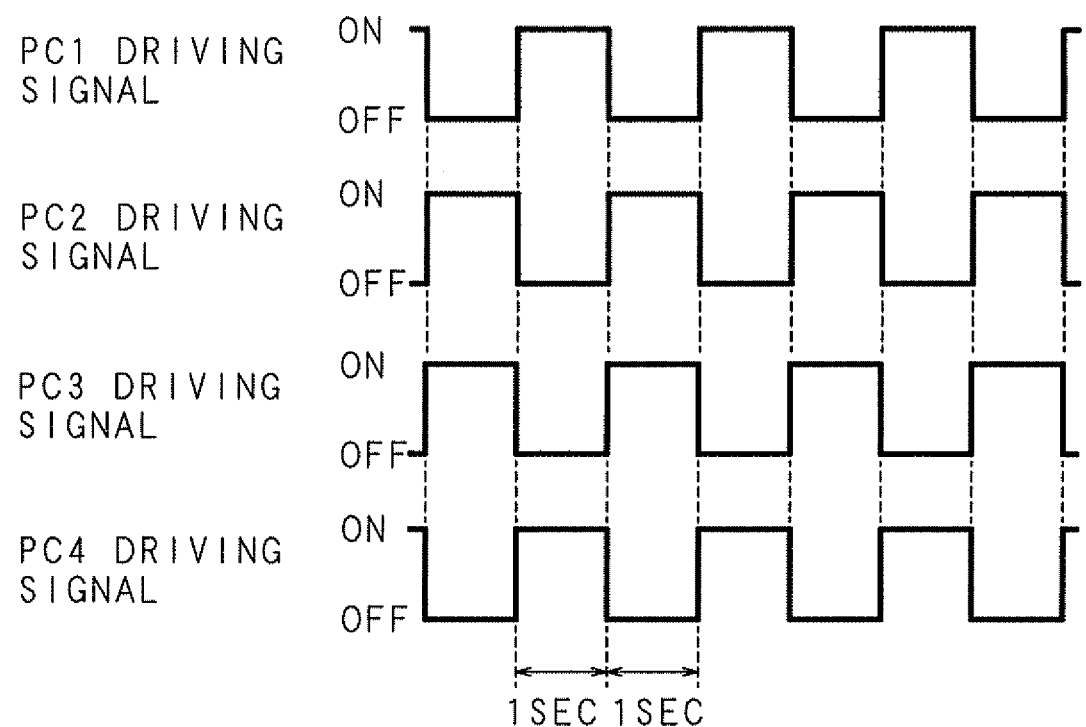
FIG. 8 is a timing chart of driving signals input from respective output interfaces to control inputs.

FIG. 8 is a timing chart of driving signals input from the respective output interfaces 88, 88, 88, 88 to the control inputs PC1, PC2, PC3, PC4. The driving signals input to the control inputs PC1 and PC2 alternately repeat "on" for one second and "off" for one second at 50% duty cycle, while the driving signals input to the control inputs PC1, PC4 and to the control inputs PC2, PC3 repeat "on" and "off" in the same phase. This makes the ion generator driving circuits 91, 91, 91, 91 alternately connect and disconnect the power supply to the respective ion generators 6a, 6d, 6b and 6c every other second. Hence, the ion generators 6a, 6d and ion generators 6b, 6c are alternately driven every other second.

Figure 9:
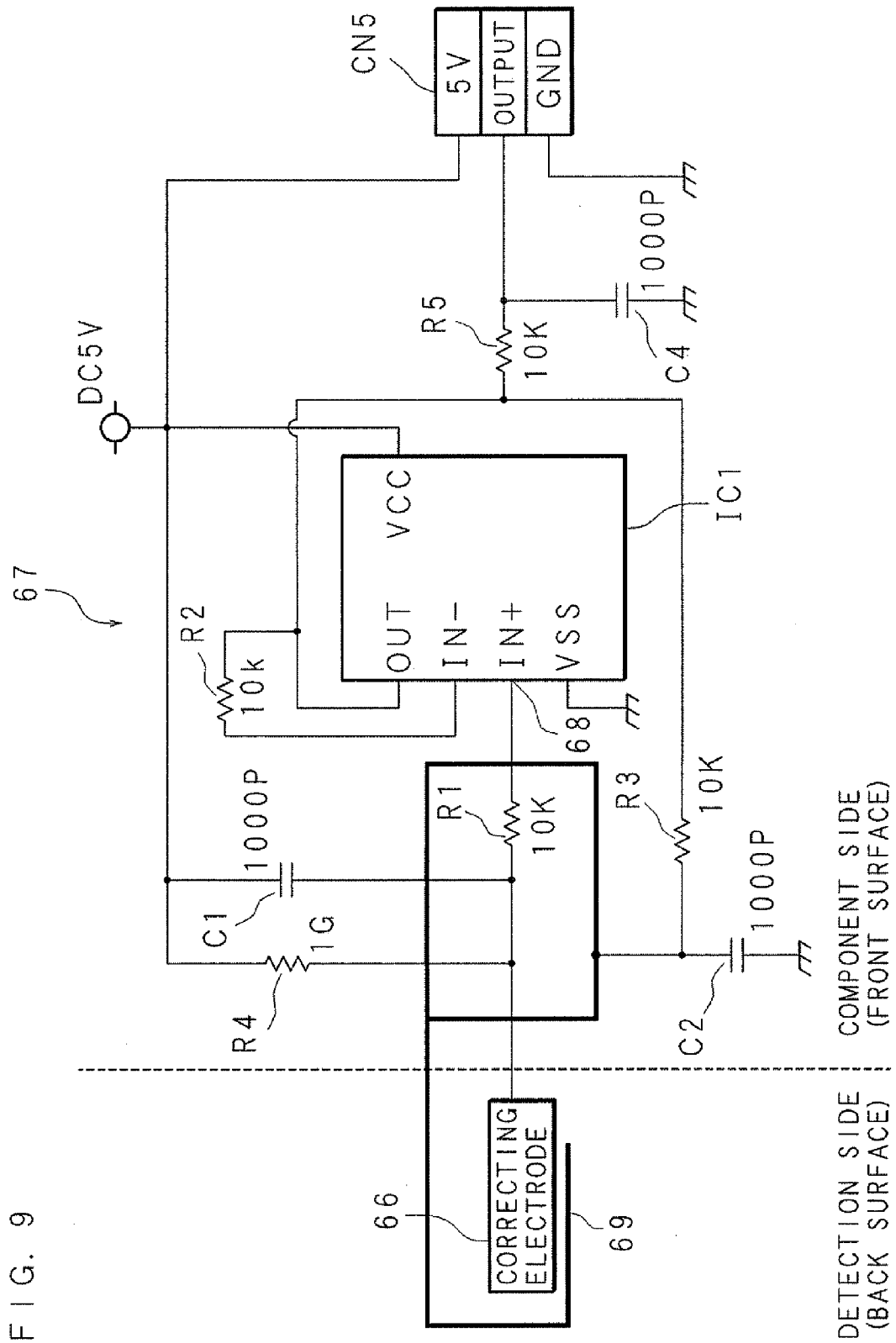
FIG. 9 is a circuit diagram illustrating the configuration of an ion detecting apparatus except for a control system.

FIG. 9 is a circuit diagram illustrating the configuration of an ion detecting apparatus except for a control system. The ion detecting apparatus includes a measurement section 67 and a collecting electrode 66 provided on the component side (front side) and the detection side (back side), respectively, of a circuit substrate which will be described later.

The measurement section 67 has a resistance R4 that pulls up the collecting electrode 66 to the 5V direct-current power supply, both terminals of the resistance R4 being connected in parallel with a condenser C1. The collecting electrode 66 is connected via a protective resistance (circuit element) R1 of the measurement section 67 to a non-inverting input 68 of an operation amplifier (converter) IC1 in which a resistance R2 is connected between the inverse input and the output.

The output of the operation amplifier IC1 is connected to the resistances R3 and R5 that are serially connected with the respective condensers C2 and C4 connected to the ground potential. The connecting point between the condenser C2 and the resistance R3 is connected to the protective electrode 69, while the connecting point between the condenser C4 and the resistance R5 is connected to the output terminal of a connector CN5. The connecter CN5 is for supplying the potential measured by the ion detecting apparatus to the A/D converting circuit 89. The protective electrode 69 encloses the collecting electrode 66 except for one part, while enclosing the protective resistance R1 and the points that are connected to both terminals of the protective resistance R1.

In the circuit described above, when negative ions are collected by the collecting electrode 66, the negative charge having negative ions charges the condenser C1 connected to the collecting electrode 66, lowering the potential of the connecting point between the condenser C1 and the protective resistance R1, the lowered potential being applied to the non-inverting input 68 of the operation amplifier IC1 via the protective resistance R1. The operation amplifier IC1 forms an impedance converter of an amplification degree of 1 with the output thereof fed back to the inverting input, the potential of the output being the same as the potential applied to the non-inverting input 68. This potential is output from the output terminal of the connector CN5 via the resistance R5 as an analog voltage value for the ground potential.

Moreover, the output impedance of the operation amplifier IC1 is a value small enough compared to the resistance value of the resistance R3, allowing the protective electrode 69 to maintain the same potential as the collecting electrode 66 via the resistance R3 having a resistance value of one hundred-thousandth (10 kΩ) of the resistance R4 (1 GΩ) which pulls up the collecting electrode. This prevents, therefore, the electric charge held by the ions collected by the collecting electrode 66 from being conducted on the surface of the circuit substrate along the path from the collecting electrode 66 to the operation amplifier IC1 and moving outside the area enclosed by the protective electrode 69.

Note that the protective resistance R1 is not limited to a resistance, but may alternatively be a series-parallel circuit of a circuit element such as a resistance, coil or the like for a purpose other than protection.

Figure 10B:
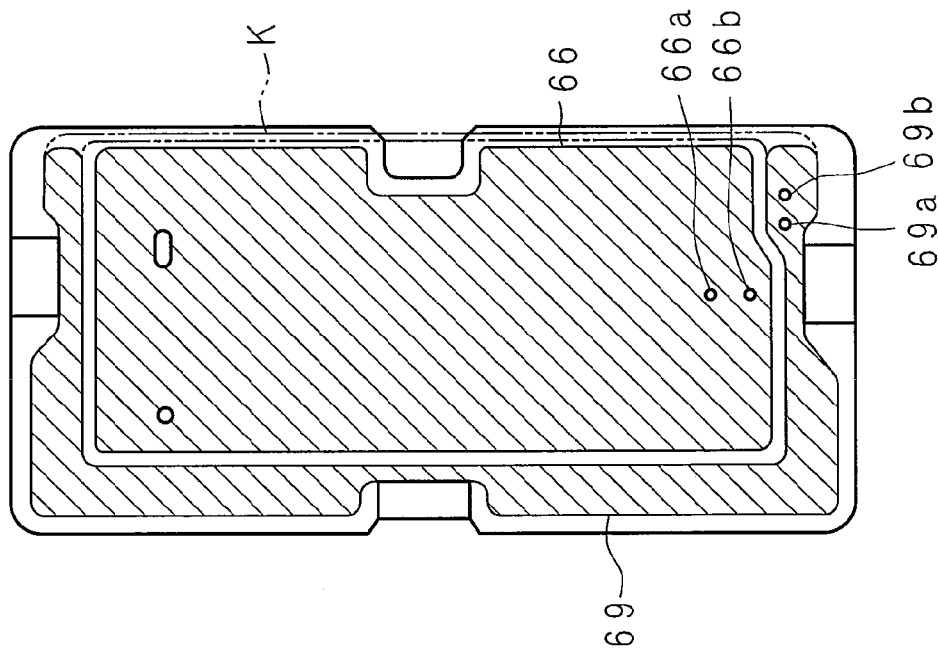
FIG. 10 is a plan view illustrating a conductor pattern of a circuit substrate of an ion detecting apparatus.
Figure 10A:
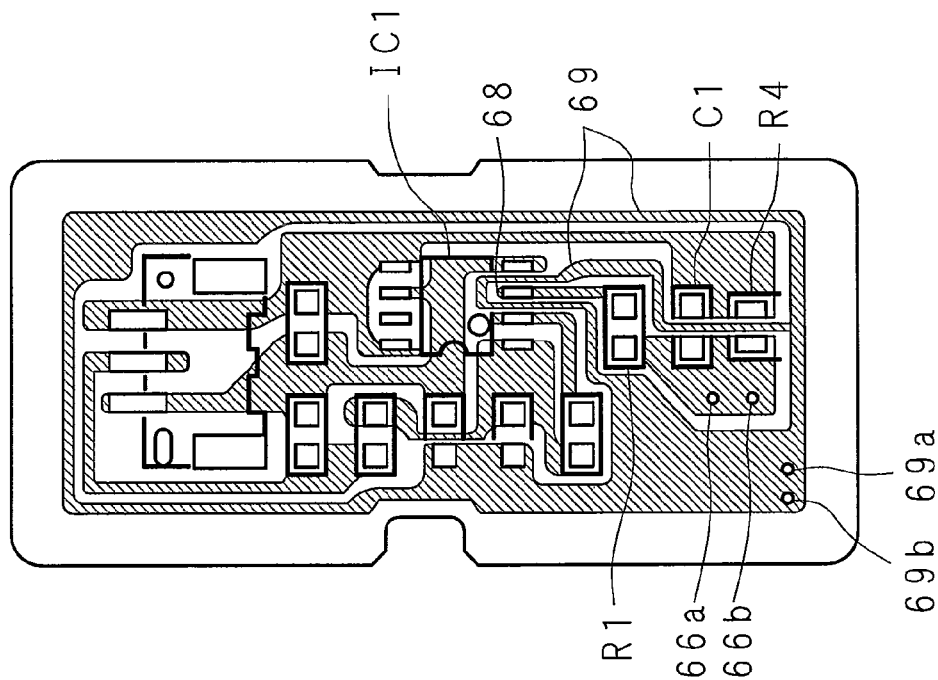

FIG. 10 is a plan view illustrating a conductor pattern of a circuit substrate of an ion detecting apparatus. FIG. 10A shows a conductor pattern of the front surface on which a circuit element is mounted, while FIG. 10B shows a conductor pattern of the back surface on which the collecting electrode 66 and the protective electrode 69 are formed. The collecting electrode 66 is electrically connected with the conductor patterns on the front surface by the through holes 66a, 66b, while one terminal of each of the protective resistance R1, resistance R4 and condenser C1 is connected to the conductor pattern.

The protective electrode 69 enclosing the collecting electrode 66 on the back surface forms an approximately laterally-facing U shape in planar view with one side in the longitudinal direction of the circuit substrate of an approximately rectangular shape having a missing portion K, and is electrically connected to the protective electrode 69 enclosing the circuit element on the front surface by the through holes 69a, 69b. The protective electrode 69 on the front surface further encloses the conductor pattern described above and a conductor pattern connecting the protective resistance R1 and the non-inverting input 68.

Since the plane configured by the above-described conductor pattern and the protective electrode 69 enclosing the protective resistance R1 is approximately in parallel with the plane configured by the collecting electrode 66, the flux leaking from the booster transformer 65 minimally interlinks with the protective electrode 69.

Figure 11:
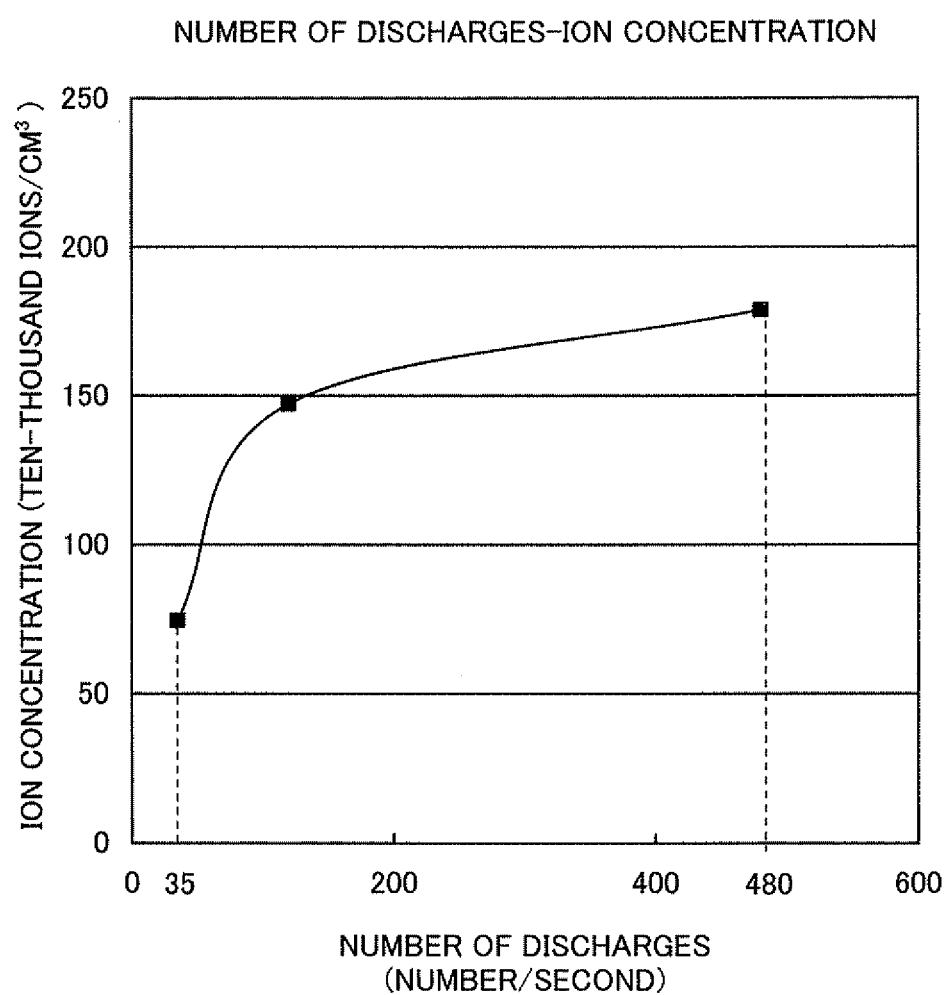
FIG. 11 is a graphic chart illustrating the concentration of negative ions with respect to the number of discharges from an ion generator.

FIG. 11 is a graphic chart illustrating the concentration of negative ions with respect to the number of discharges from the ion generator 6a (or 6b, 6c, 6d). The horizontal axis in the chart indicates the number of discharges per unit of time (number of discharges/second), while the vertical axis indicates the concentration of negative ions (10,000 ions/cm$^3$) at a position separated by 25 cm above the upper surface of the wind directing body 7 from which ions are discharged with air. The ion concentration obtained at 480 discharges/second, which is the standard number of discharges, corresponds to approximately 1,800,000 ions/cm$^3$. When the number of discharges is 35, for example, the ion concentration of a value slightly exceeding one half of 1,800,000 ions/cm$^3$ may be obtained. Here, the ion concentration corresponding to 35 discharges as described above is set, by way of example, as the number of discharges corresponding to the lower limit of the ion concentration which should be detected as ion existing.

FIG. 12 is a graphic chart illustrating the variation amount of an electric potential measured by the ion detecting apparatus before and after discharge with respect to the number of discharges from the ion generator 6a (or 6b, 6c, 6d). The horizontal axis in the chart indicates the number of discharges per unit of time (discharges/second), while the vertical axis indicates the variation in potential (V) of the output terminal of the connector CN5. The broken line shows the variation in potential when the surrounding temperature/humidity is 26° C./48%, while the solid line shows the variation in potential at 40° C./90%.

When the horizontal axis in the graph of FIG. 12 takes the number of discharges set in FIG. 11 by way of example (35 discharges), the variation in potential obtained at the surrounding temperature/humidity of 26° C./48% and 40° C./90% can be read as 3.3V and 0.8V, respectively. Here, the above-described 40° C./90% is set as the worst case in the environment in which ions should be detected. Ions are to be detected as existing until the variation in potential is reduced to 0.5V, which is even lower by 40% than 0.8V described above.

Figure 13:
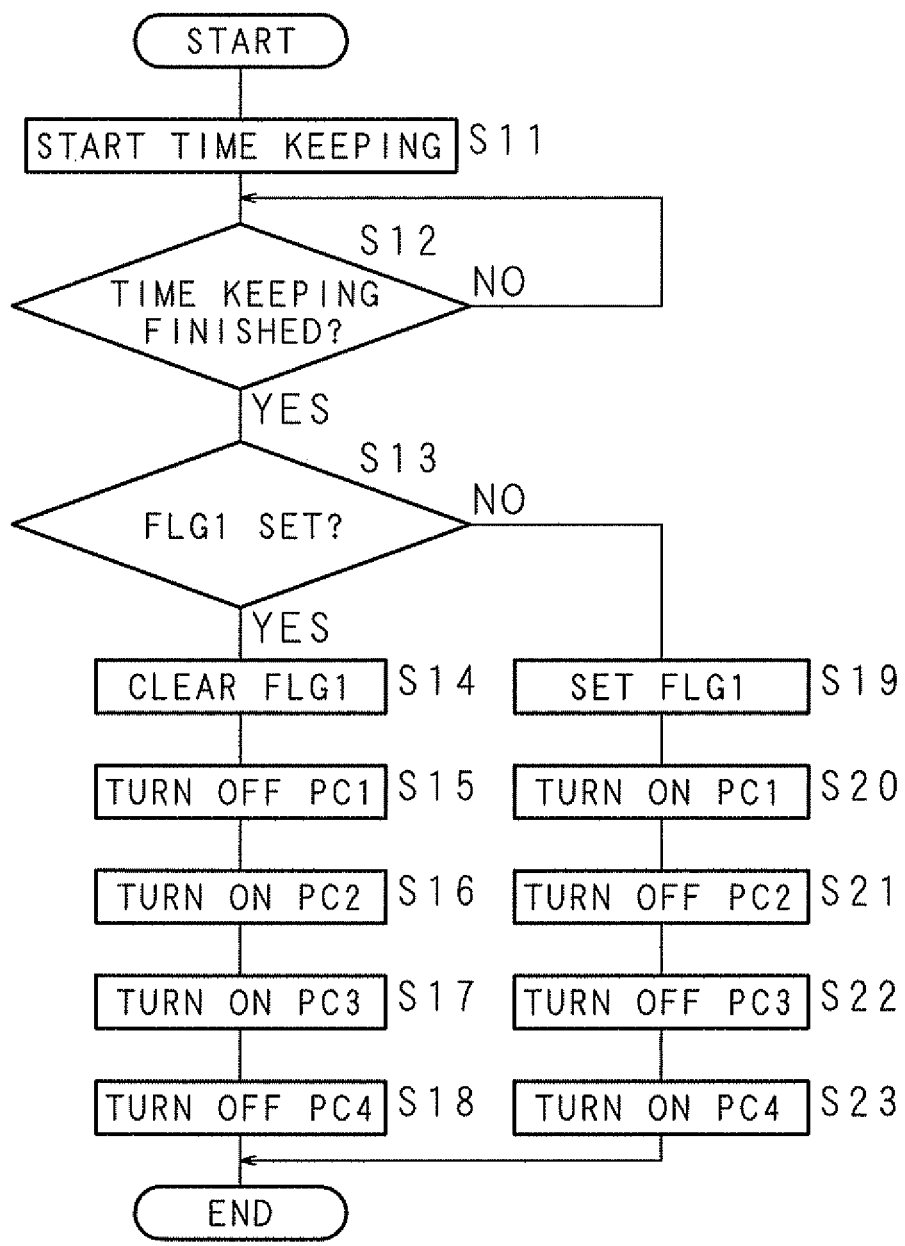
FIG. 13 is a flowchart illustrating a processing procedure of CPU that drives an ion generator.

FIG. 13 is a flowchart illustrating a processing procedure of the CPU 81 that drives the ion generators 6a, 6b, 6c and 6d. The processing below is executed as needed in accordance with a control program stored in the ROM 82 in advance, and is executed again every time the processing is terminated. Note that the contents of FLG1 indicating on/off phase are stored in the RAM 83.

The CPU 81 makes the timer 84 start keeping time for one second (step S11). The time kept is not limited to one second, but may also be 0.5 seconds, 1.5 seconds or the like. Subsequently, the CPU 81 determines whether or not the timer 84 has finished the time keeping (step S12). If it is determined that the time keeping is not finished (NO at step S12), the CPU 81 waits until the timer 84 finishes time keeping. If it is determined that the time keeping is finished (YES at step S12), the CPU 81 determines whether or not FLG 1 is set (step S13).

If it is determined that FLG 1 is set (YES at step S13), the CPU 81 clears the FLG 1 (step S14) and inverts it. Subsequently, the CPU 81 turns off the output of one output interface 88 to turn off the control input PC1 of the ion generator driving circuit 91 (step S15). Likewise, the CPU 81 turns on the control input PC2 (step S16) and turns on the control input PC3 (step S17), while it turns off the control input PC4 (step S18) and terminates the processing.

If it is determined that FLG1 is not set at step S13 (NO at step S13), the CPU 81 sets the FLG 1 (step S19). Subsequently, the CPU 81 turns on the output of one output interface 88 and turns on the control input PC1 of the ion generator driving circuit 91 (step S20). Likewise, the CPU 81 turns off the control input PC2 (step S21) and turns off the control input PC3 (step S22), while it turns on the control input PC4 (step S23) and terminates the processing.

Figure 14:
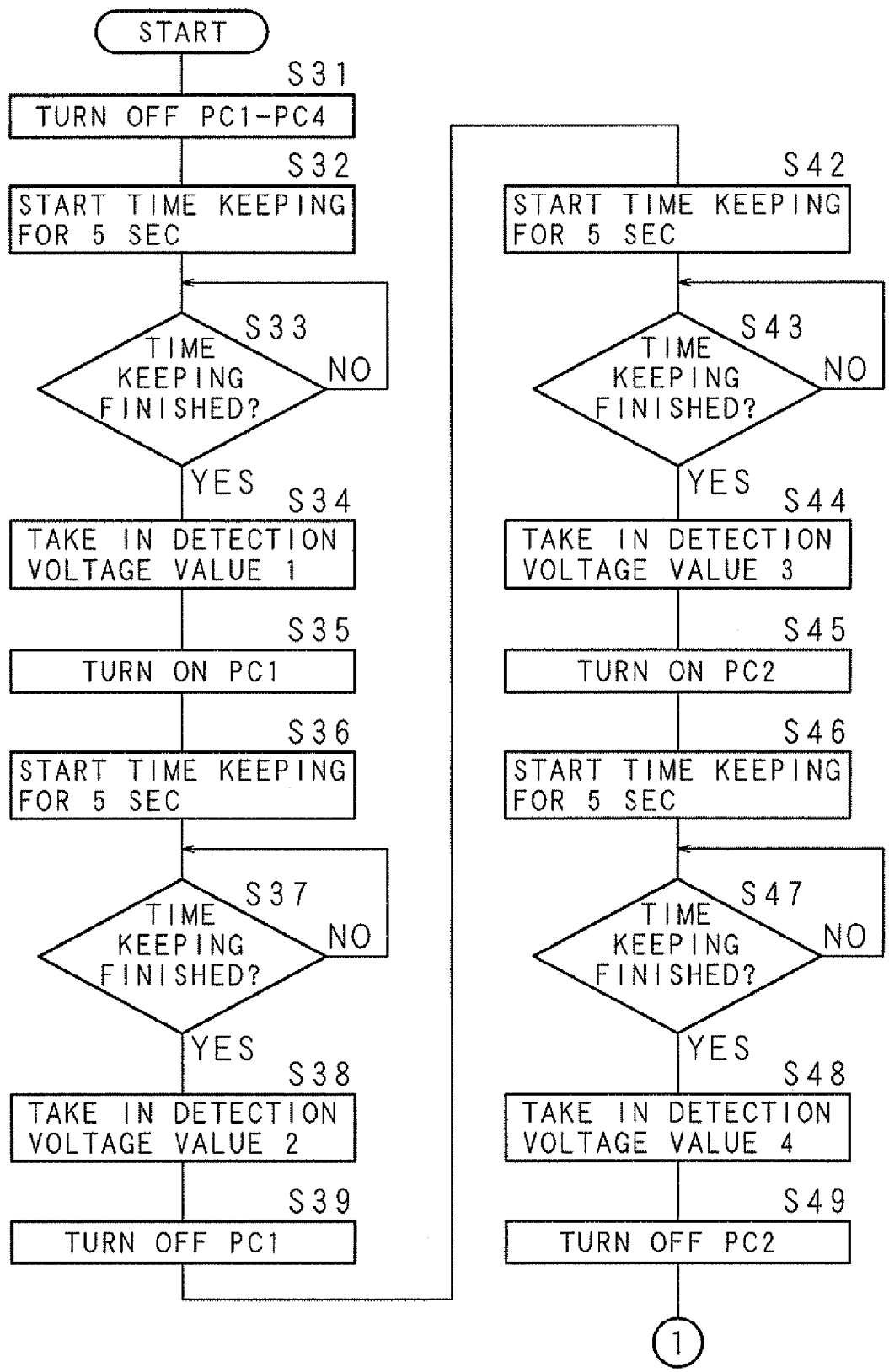
FIG. 14 is a flowchart illustrating a processing procedure of CPU that outputs a warning based on a result of detection of negative ions.
Figure 15:
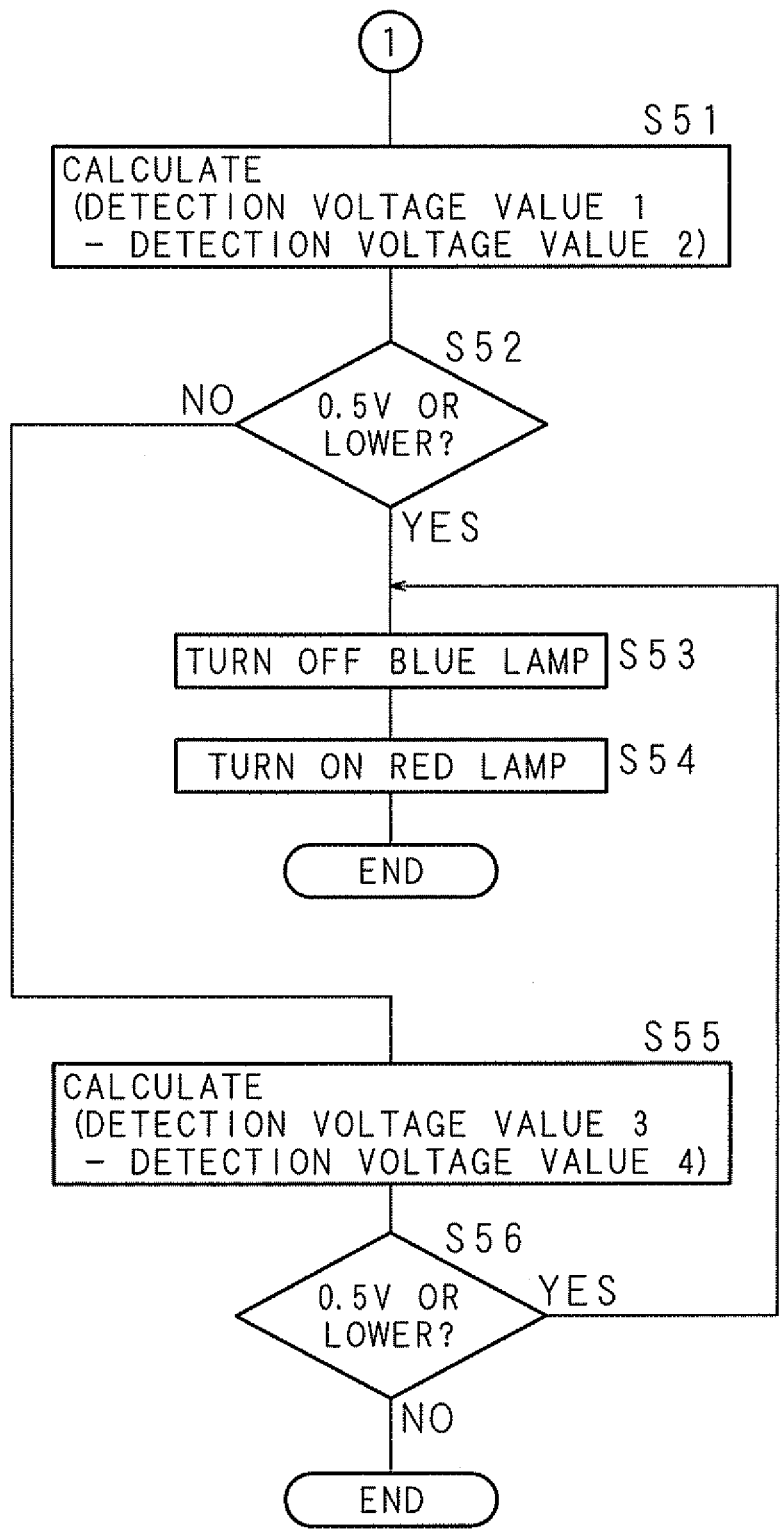
FIG. 15 is a flowchart illustrating a processing procedure of CPU that outputs a warning based on a result of detection of negative ions.

FIGS. 14 and 15 are flowcharts illustrating the processing procedure of the CPU 81 that outputs a warning based on a result of detection of negative ions. The processing below is executed periodically (for example, in a ten-minute cycle) with the processing of FIG. 13 stopped, in accordance with a control program stored in the ROM 82 in advance. Note that the cycle is not limited to ten minutes, but may be arbitrary period of time. Moreover, the detected voltage values 1 to 4 are stored in RAM 83.

The CPU 81 turns off, prior to ion detection, all of the control inputs PC1, PC2, PC3, PC4 in order to make the ion generators 6a, 6b, 6c, 6d stop driving (step S31). Subsequently, the CPU 81 makes the timer 84 start time keeping for five seconds (step S32), and determines whether or not the timer 84 has finished time keeping (step S33). Note that the five seconds here corresponds to the time for waiting until the potential of the collecting electrode 66 is sufficiently pulled-up at the resistance R4, which is not limited to five seconds. If it is determined that the time keeping has not been finished (NO at step S33), the CPU 81 waits until the timer 84 finishes time keeping.

When it is determined that the time keeping has been finished (YES at step S33), the CPU 81 takes in the potential measured by the measurement section 67 via the A/D converting circuit 89 as a detection voltage value 1 (step S34). The CPU 81 then turns on the control input PC1 via the output I/F 88 so as to drive the ion generator 6a (step S35). Next, the CPU 81 makes the timer 84 start time keeping for five seconds (step S36), and determines whether or not the timer 84 has finished time keeping (step S37). It is noted that the five seconds here corresponds to the time for waiting until the potential of the collecting electrode 66 reaches a stationary value, and is not limited to five seconds.

When it is determined that the time keeping has not been finished (NO at step S37), the CPU 81 waits until the timer finishes time keeping. If it is determined that the time keeping has been finished (YES at step S37), the CPU 81 takes in the potential measured by the measurement section 67 via the A/D converting circuit 89 as a detection voltage value 2 (step S38), and turns off the control input PC1 via the output I/F 88 (step S39).

The processing from the step S32 to the step S39 described above are for storing changes in the potential of the collecting electrode 66 by the ions generated by the ion generator 6a. The potentials measured before and after generation of ions are taken in as the detection voltage value 1 and detection voltage value 2, respectively, and stored in the RAM 83.

Subsequently, the CPU 81 executes the processing from the step S42 to the step S49 to store changes in the potential of the collecting electrode 66 by the ions generated by the ion generator 6b. Here, the potentials measured before and after generation of ions are taken in as detection voltage value 3 and detection voltage value 4, respectively, and stored in the RAM 83. Moreover, at the steps S45 and S49, the control input PC2 is turned on and off, respectively. Since the other processing procedures from the steps S42 to S48 are the same as the ones from the steps S32 to S38, description thereof will not be repeated.

Next, the CPU 81 subtracts the detection voltage value 2 from the detection voltage value 1 (step S51) and determines whether or not the calculated value is equal to or lower than 0.5V (step S52). If it is determined that the value is equal to or lower than 0.5V (YES at step S52), the CPU 81 turns off a blue lamp on the display section 86 (step S53) to notify that the detection level of negative ions becomes equal to or lower than a threshold value (step S53) while it turns on a red lamp indicating a warning (step S54) and terminates the processing.

If it is determined that the calculated value is not equal to or lower than 0.5 V at step S52 (NO at step S52), the CPU 81 subtracts the detection voltage value 4 from the detection voltage value 3 (step S55), and determines whether or not the calculated value is equal to or lower than 0.5V (step S56). If it is determined that the value is equal to or lower than 0.5V (YES at step S56), the CPU 81 returns the processing back to step S53 to notify that there is abnormality. If it is determined that the calculated value is not equal to or lower than 0.5V (NO at step S56), the CPU 81 terminates the processing.

As described above, according to the present embodiment, the protective electrode is made to enclose the collecting electrode, preventing the charge held by the ions collected by the collecting electrode from being conducted through the portion where the insulation is degraded due to contamination such as dust or moisture in the surrounding air and moving outside the area enclosed by the protective electrode. Hence, ions can be detected with a high degree of accuracy.

Moreover, the missing portion K provided on one side in the longitudinal direction of the U-shaped protective electrode enclosing the approximately-rectangular collecting electrode formed on the circuit substrate is directed toward the flowing direction of the air in which negative ions are to be detected. This prevents positive ions from being collected by the collecting electrode and prevents negative ions from being collected by the protective electrode. Hence, ions can be detected with a higher degree of accuracy.

Furthermore, the protective electrode is connected to the output terminal of the operation amplifier forming the impedance converter to achieve approximately the same potential as the potential of the collecting electrode, preventing the charge held by the ions collected by the collecting electrode from being conducted through the inner side of the area enclosed by the protective electrode and moving to the protective electrode. Hence, ions can be detected with a higher degree of accuracy.

Furthermore, a protective resistance is provided between the collecting electrode and the operation amplifier, while the conductor pattern of the protective electrode encloses both terminals of the protective resistance and the conductor pattern connected to the both terminals. This can prevent the operation amplifier from being directly applied with high voltage caused by static electricity or the like. Moreover, the conductor pattern formed from the collecting electrode through the protective resistance to the non-inverting input is enclosed by the protective electrode, allowing ions to be detected with a higher degree of accuracy.

Furthermore, the collecting electrode is pulled up to DC 5V by a resistance, so that the potential of the collecting electrode is lowered when the collecting electrode collects negative ions, and the negative ions are detected. Therefore, for example, at the negative ion generating section to which foreign materials such as silicon are easily attached to the electrode thereof and the amount of generated ions tends to decrease, abnormality in the amount of generated ions can be detected.

Furthermore, the measurement section is arranged on the front surface of the circuit substrate while the collecting electrode is arranged on the back surface thereof, and the protective electrode encloses the measurement section.

Accordingly, the collecting electrode is connected to the measurement section with a minimum distance, suppressing unnecessary moving of electric charge while reducing the whole size of the ion detecting apparatus. Moreover, the charge held by the ions collected by the collecting electrode can be prevented from moving to the measurement section, allowing ions to be detected with a higher degree of accuracy.

Furthermore, based on the result of detection of ions generated by the ion generator, a warning is outputted to the user by LED on the display section. Hence, the user can be notified of lowering of the amount of generated ions, and be urged to clean the ion generating section or to exchange the ion generator.

Furthermore, the collecting electrode is provided in the vicinity of the ion generator which is directed to the direction in which the flux leaking from the booster transformer minimally interlinks with the collecting electrode. This allows ions to be detected with a high degree of accuracy and the high voltage raised by the booster transformer to be stabilized.

Furthermore, the ion detecting apparatus is directed to the direction in which the flux leaking from the booster transformer of the ion generator minimally interlinks with the portion enclosed by the conductor pattern of the protective electrode. This allows the high voltage raised by the booster transformer to be stabilized.

It is noted that, though in Embodiment 2, the potential of the collecting electrode is measured by sequentially turning on and off the control input PC1 and the control input PC2, It is not limited thereto. It may also be possible, for example, to sequentially turn on and off the control input PC1 and the control input PC4, and to sequentially turn on and off the control input PC2 and the control input PC3.

Moreover, though the collecting electrode is pulled up to DC 5V by a resistance to detect negative ions, it is not limited thereto. It may also be possible to pull down the electrode to the ground potential by a resistance to detect positive ions. In such a case, the collecting electrode is arranged in the vicinity of the positive ion generating section, while the sign of the calculated value may be inverted at the step S51 and step S55 of FIG. 15.

Furthermore, though a red lamp on the display section is turned on as a warning, it is not limited thereto. It may also be possible to provide a buzzer to emit (output) an alarming sound, or to provide a voice synthesis circuit and a speaker to emit an alarming voice.

Furthermore, though the protective electrode encloses the collecting electrode and the measurement section, it is not limited thereto. For example, a portion close to the collecting electrode may be connected to the protective electrode to eliminate static electricity in the duct.

Embodiment 3

Figure 16:
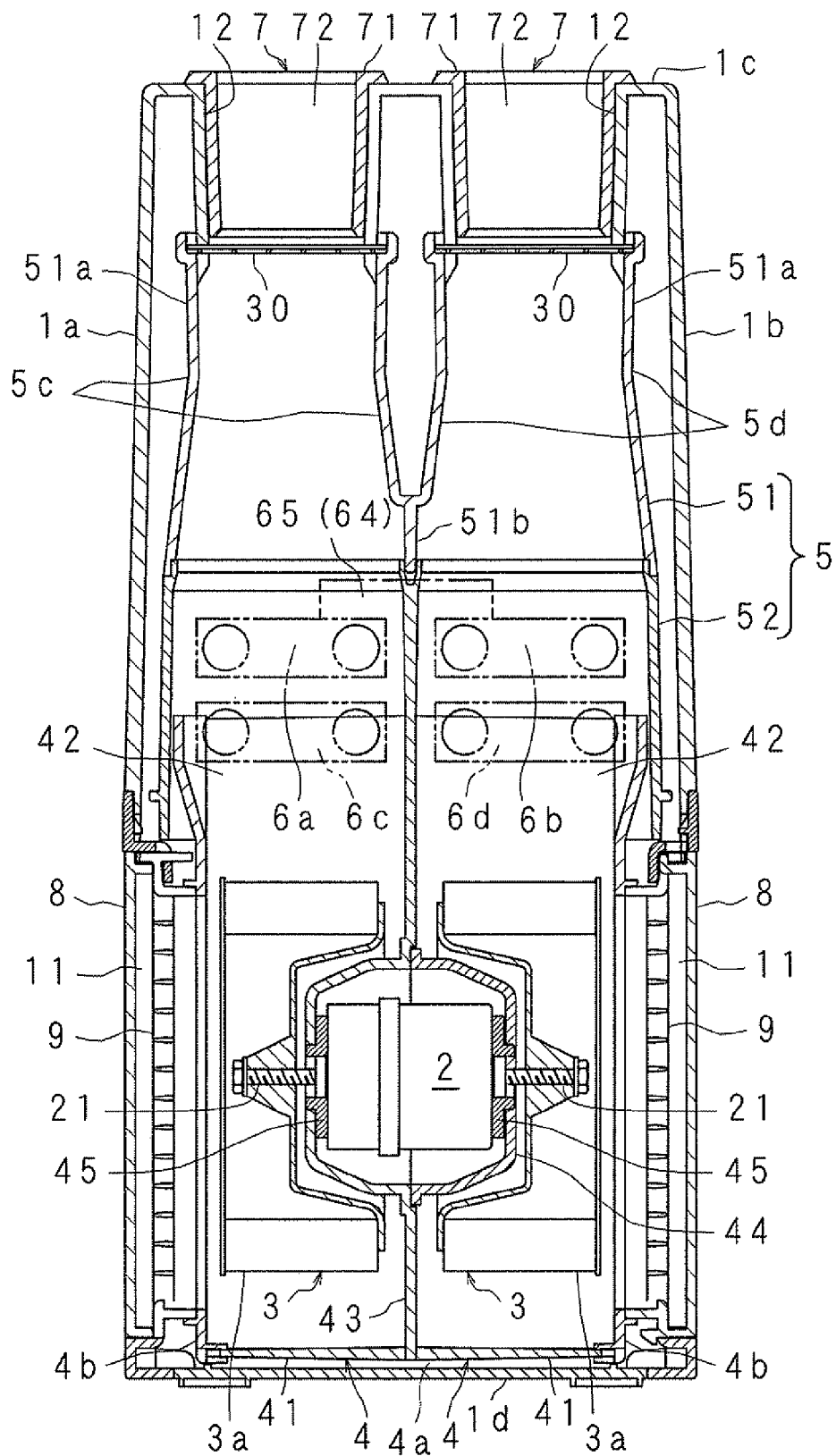
FIG. 16 is a vertical section front view illustrating the configuration of an ion generating apparatus according to the present invention.
Figure 17:
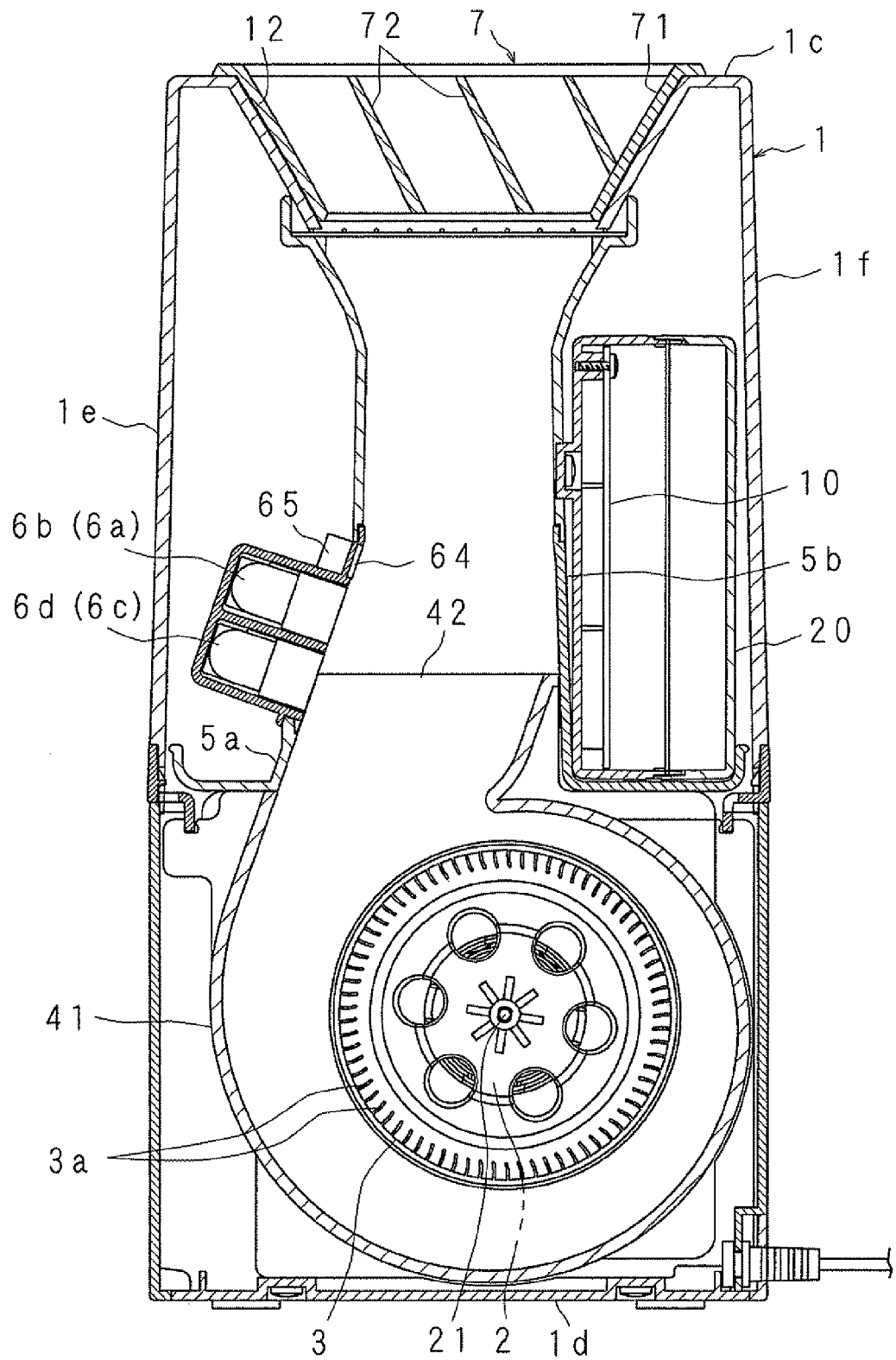
FIG. 17 is a vertical section side view illustrating the configuration of an ion generating apparatus.
Figure 18:
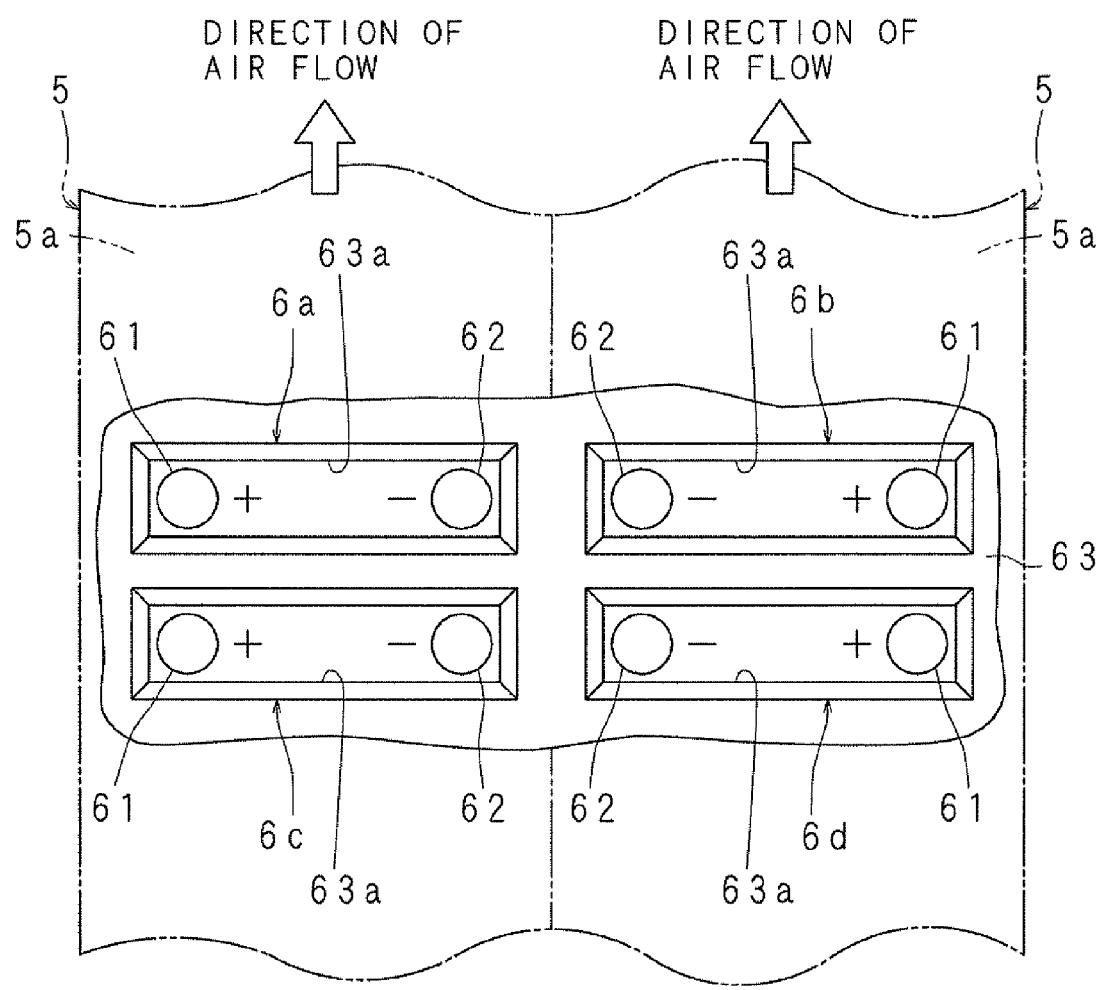
FIG. 18 is a schematic front view illustrating a state where an ion generator is attached on a front wall.

The present invention will be described based on the drawings illustrating an embodiment thereof. FIG. 16 is a vertical section front view illustrating the configuration of an ion generating apparatus according to the present invention. FIG. 17 is a vertical section side view illustrating the configuration of an ion generating apparatus. FIG. 18 is a schematic front view illustrating a state where the ion generators 6*a*, 6*b*, 6*c* and 6*d* are attached on the front wall 5*a*.

A housing is denoted by the numeral 1 in the drawings, the housing 1 including both side walls 1*a*, 1*b* separated from and opposed to each other having suction ports 11, 11 at a lower part thereof, and a top wall 1*c* having two engagement holes (discharge ports) 12, 12 at the central portion thereof. At the lower portion in the housing 1, a motor 2 having output shafts 21, 21 on both sides of the direction of the rotating axis is arranged, two impellers 3, 3 housed in two casings 4, 4 to be freely rotatable being mounted, respectively, on the output shafts 21, 21 of the motor 2.

Above the impellers 3, 3, two ducts 5, 5 are arranged, respectively, as tubular portions letting the air generated by the rotations individually flow upward. The ducts 5, 5 have, at lower portions thereof, ion generators 6*a*, 6*c*, 6*b*, 6*d* each having two ion generating sections 61, 62, and are provided with wind directing bodies 7, 7 arranged at the engagement holes 12, 12 to be removable. Above the ion generators 6*a*, 6*b*, an ion sensor (detection means) 64 for detecting generated ions and an ion detecting circuit (detecting means) 65 for detecting the potential of the ion sensor 64 are arranged to be adjacent to the ion generators 6*a* and 6*b*. Note that the motor 2, impellers 3, 3 and casings 4, 4 constitute an air blower.

The housing 1 further includes a bottom wall 1*d* of a rectangular shape in a planar view, a front wall 1*e* and a back wall 1*f* continuing into two sides, front and back, of the bottom wall 1*d*, and forms an approximately rectangular parallelepiped. At the lower portion of the front wall 1*e*, an operation portion 85 and a display section (warning means)

86, which will be described later, are arranged (not illustrated). To the suction ports 11, 11 at the lower parts of the both side walls 1a, 1b, filters 8, 8 that let through the air suctioned from the suction ports 11, 11 by the impellers 3, 3 and eliminate foreign materials in the air to clean the air are attached. Each of the engagement holes 12, 12 on the top wall 1c forms a rectangular shape with the longitudinal direction thereof being front and back, the inner surface on the front side being tilted forward relative to the vertical direction, and the inner surface on the back side being tilted backward relative to the vertical direction. Moreover, the housing 1 is divided into an upper body and a lower body at the middle part thereof in the up-down direction. The casings 4, 4 are mounted on the lower body while the ducts 5, 5 are mounted on the upper body.

The impellers 3, 3 are multi-blade impellers having a plurality of blades 3a with the side of its rotating center displaced in the rotating direction relative to the outer edge. In other words, they are Sirocco impellers (Sirocco fans) having a circular cylinder shape. One end of each of the impellers 3, 3 has a bearing board. Each of the output shafts 21, 21 of the motor 2 is placed at a shaft hole opened at the center of the bearing board, which functions such that the air taken in from an opening at the other end to an air hole at the center is released from between the blades 3a on the outer circumference.

The casings 4, 4 have circular-arc guide walls 41, 41 that guide the airflow generated by rotation of the impellers 3, 3 in the rotating direction to increase the speed of the airflow, and blowing ports 42, 42 opened upward from a part of the circular-arc guide walls 41, 41 to one direction of the tangent lines of the circular-arc guide walls 41, 41. Each of the blowing ports 42, 42 forms a square-tubular shape that protrudes from a part of the circular-arc guide walls 41, 41 in the direction of tangent lines of the circular-arc guide walls 41, 41 and in the direction diagonal to the vertical direction.

Moreover, the casings 4, 4 form the shape of deep dishes, including casing bodies 4a, 4a having the circular-arc guide walls 41, 41 and openings for blowing ports 42, 42, and including cover plates 4b, 4b on which the portions corresponding to the openings of the impellers 3, 3 are opened and which close the open side of the casing bodies 4a, 4a. The opposing sides of the casing bodies 4a, 4a are connected together by a joint wall (diversion body) 43 for partitioning. Furthermore, ventilation plates 9, 9 having a plurality of ventilation holes are provided between the open portions of the cover plates 4b, 4b and filters 8, 8.

The portion corresponding to the motor 2 at the joint wall 43 has a concave which is dent toward the side of one casing body 4a, while a support plate 44 of a deep-dish shape is attached to the edge of the concave. Rubber plates 45, 45 are placed between the concave and the central part of the support plate 44 to hold the motor 2 in a sandwiched manner. Each of the output shafts 21, 21 is inserted through the shaft hole opened at the concave and the central part of the support plate 44, the impellers 3, 3 being attached to the output shafts 21, 21. Moreover, the upper end of the joint wall 43 is extended to above the casings 4, 4.

The ducts 5, 5 are formed of a tube section having a square-tubular shape, the lower ends thereof continuing into the blowing ports 42, 42, the upper ends thereof continuing into the engagement holes 12, 12, and the middle part thereof in the up-down direction being narrowed down. Moreover, the ducts 5, 5 have front walls 5a, 5a arranged along one direction of the tangent line extending from the blowing ports 42, 42 to the circular-arc guide walls 41, 41, and back walls 5b, 5b arranged approximately vertical from the blowing ports 42, 42. Two sets of approximately-vertically-arranged side walls 5c, 5c, 5d, 5d continue from the front walls 5a, 5a and back walls 5b, 5b. The ducts 5, 5 are configured such that the air blown from the blowing ports 42, 42 becomes laminar flow along the front walls 5a, 5a and side walls 5c, 5c, 5d, 5d and flows vertically along the walls.

At the front walls 5a, 5a, penetration holes corresponding to the ion generating sections 61, 62 are opened, while the ion generators 6a, 6b, 6c, 6d are engaged to be attached to the penetration holes. On the back walls 5b, 5b, a circuit substrate 10 connected to the motor 2, ion generators 6a, 6b, 6c, 6d, ion sensor 64 and a power line, as well as a cover 20 covering the circuit substrate 10 are mounted.

Moreover, the ducts 5, 5 are divided into a duct upper body 51 and a duct lower body 52 at the middle part thereof in the up-down direction. The duct lower body 52 forms a square tubular shape and partitioned at the center thereof in the horizontal direction by the joint wall 43. For the duct upper body 51, the lower part of the square tube sections 51a, 51a separately arranged in parallel with each other in the horizontal direction forms one continuing portion at the joint section (diversion body) 51b, and is partitioned by the joint section 51b and the joint wall 43. Moreover, at the upper end of the duct upper body 51, protection nets 30, 30 are arranged for preventing foreign materials such as a finger from being inserted from the outside.

The wind directing bodies 7, 7 have square frame portions 71, 71 with an inverse-trapezoid cross-sectional shape in the front-back direction, and a plurality of wind directing boards 72, 72 that are separately arranged in parallel with each other in the front-back direction in the square frame portions 71, 71 and tilted toward one front-back direction relative to the vertical direction, and are formed in the same shape. The front and back walls of the square frame portions 71, 71 are tilted in the front-back direction relative to the vertical direction.

Each of the ion generators 6a, 6b, 6c, 6d includes two ion generating sections 61, 62 separately arranged in the direction approximately perpendicular to the flowing direction of air generated by rotation of the impellers 3, 3. Each of the ion generating sections 61, 62 has at the inner rear side thereof a discharge electrode and a guide electrode surrounding the discharge electrode, the discharge electrode applied with high voltage generating a corona discharge. Accordingly, one ion generating section 61 generates positive ions while the other ion generating section 62 generates negative ions.

The ion generators 6a, 6b, 6c, 6d are held by a holder 63 and attached to the front walls 5a, 5a of the respective ducts 5, 5. In each of the two sets of the ion generators 6a, 6b and the ion generators 6c, 6d, the negative ion generating sections 62 are arranged to be facing each other, while a set of ion generators are arranged to be adjacent to each other in the direction approximately perpendicular to the air-flowing direction. The sets of generators are separately arranged in parallel with each other in the air-flowing direction. The ion generating sections 61, 62 of each of the ion generators 6a, 6b, 6c, 6d face to the duct 5,5 from the penetration holes. Moreover, the side of the holder 63 to which the ducts 5, 5 are attached have four openings corresponding to the ion generating sections 61, 62, while the ion generating sections 61, 62 are arranged at each of the openings 63a, . . . , 63a.

The ion sensor 64 is formed by a plate-like electrode of an approximately rectangular shape collecting ions, its electrode surface being exposed into the ducts 5, 5 such that negative ions generated by the ion generating sections 62, 62 of the ion generators 6a, 6b may be detected in the proximity thereof. When the ion sensor 64 collects negative ions, the potential of the ion sensor 64 is lowered. The potential of the ion sensor 64 may be detected at the ion detection circuit 65 as a voltage value for the ground potential. Though the ion sensor 64 is arranged in the proximity to the ion generating sections (areas where ions are generated) 62, 62, it is not limited thereto. It may also be arranged, for example, at an arbitrary portion on the inner surface of the engagement holes (area where ions are discharged) 12 or at an arbitrary portion on the side walls 1a, 1b, top wall 1c, front wall 1e or back wall 1f of the housing 1 (a given portion outside).

The ion generating apparatus configured as described above is installed in a residential room. The motor 2 of the air blower is driven to rotate the impellers 3, 3, which suctions the air in the room from the suction ports 11, 11 on both sides into the two casings 4, 4, and the foreign materials such as dust in the suctioned air are eliminated by the filters 8, 8. Here, the air suctioned into the casings 4, 4 becomes laminar flow by the circular-arc guide walls 42, 42 around the impellers 3, 3, the laminar airflow passing through along the circular-arc guide walls 41, 41 to the blowing ports 42, 42, which blow the air into the ducts 5, 5.

Figure 19:
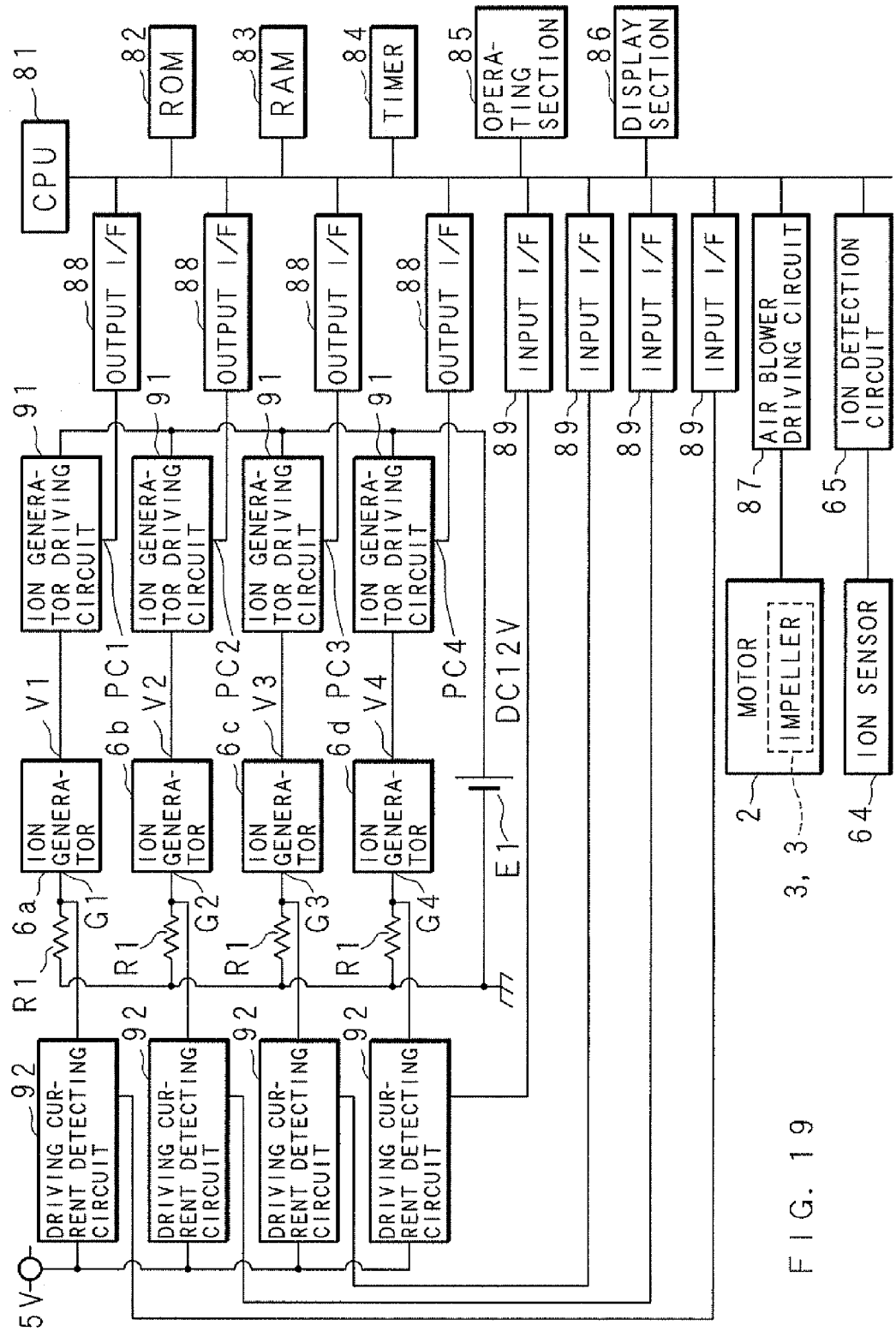
FIG. 19 is a block diagram illustrating the schematic configuration of a control system in an ion generating apparatus.

FIG. 19 is a block diagram illustrating the schematic configuration of a control system in an ion generating apparatus. Serving as the center of the control system is the CPU 81 which is connected by bus interconnection with a ROM 82 storing information such as a program and the like, a RAM 83 storing temporarily-generated information and a timer 84 for keeping time. The CPU 81 executes processing such as input/output, calculation and the like in accordance with the control program stored in the ROM 82 in advance.

Further connected by bus interconnection with the CPU 81 are: an operating section 85 for receiving operation to change the air volume of the ion generating apparatus; a display section 86 constituted by an LED which displays information such as a warning, an operating condition and the like; an air-blower driving circuit 87 for driving the motor 2 on which the impellers 3, 3 are mounted; and an ion detection circuit 65 connected to the ion sensor 64.

The output sides of the output interfaces 88, 88, 88, 88 connected by bus interconnection with the CPU 81 are connected to control inputs PC1, PC2, PC3, PC4 of the ion generator driving circuits 91, 91, 91, 91, respectively. One ends of the respective outputs of the ion generator driving circuits 91, 91, 91, 91 are connected to the positive electrode of a 12V direct-current power supply E1, the negative electrode of which is connected to the ground potential. The other ends are connected to the power inputs V1, V2, V3 and V4 of the ion generators 6a, 6b, 6c and 6d.

The ground inputs G1, G2, G3, G4 of the respective ion generators 6a, 6b, 6c, 6d are connected to the ground potential via resistances R1, R1, R1, R1 for detecting driving current (means for detecting current). The points of connection between the ground inputs G1, G2, G3, G4 and the resistances R1, R1, R1, R1 are connected, respectively, to the inputs of the driving current detecting circuits (means for detecting current) 92, 92, 92, 92 connected to the power supply of DC 5V. The detection outputs of the driving current detecting circuits 92, 92, 92, 92 are connected to the input sides of the input interfaces 89, 89, 89, 89, respectively, that are connected to the CPU 81 by bus interconnection.

In the configuration as described above, every time the timer 84 times a given time, the CPU 81 inverts on/off of the control inputs PC1, PC2, PC3 and PC4 of the ion generator driving circuits 91, 91, 91, 91 via the output interfaces 88, 88, 88, 88. This makes the ion generator driving circuits 91, 91, 91, 91 connect/disconnect the connection between the power inputs V1, V2, V3, V4 of the respective ion generators 6a, 6b, 6c, 6d and the positive electrode of the direct-current power supply E1 at every given time. Moreover, the driving current detecting circuits 92, 92, 92, 92 detect, respectively, whether or not the current flowing when the ion generators 6a, 6b, 6c, 6d are driven corresponds to a value equal to or larger than a given value.

Figure 20:
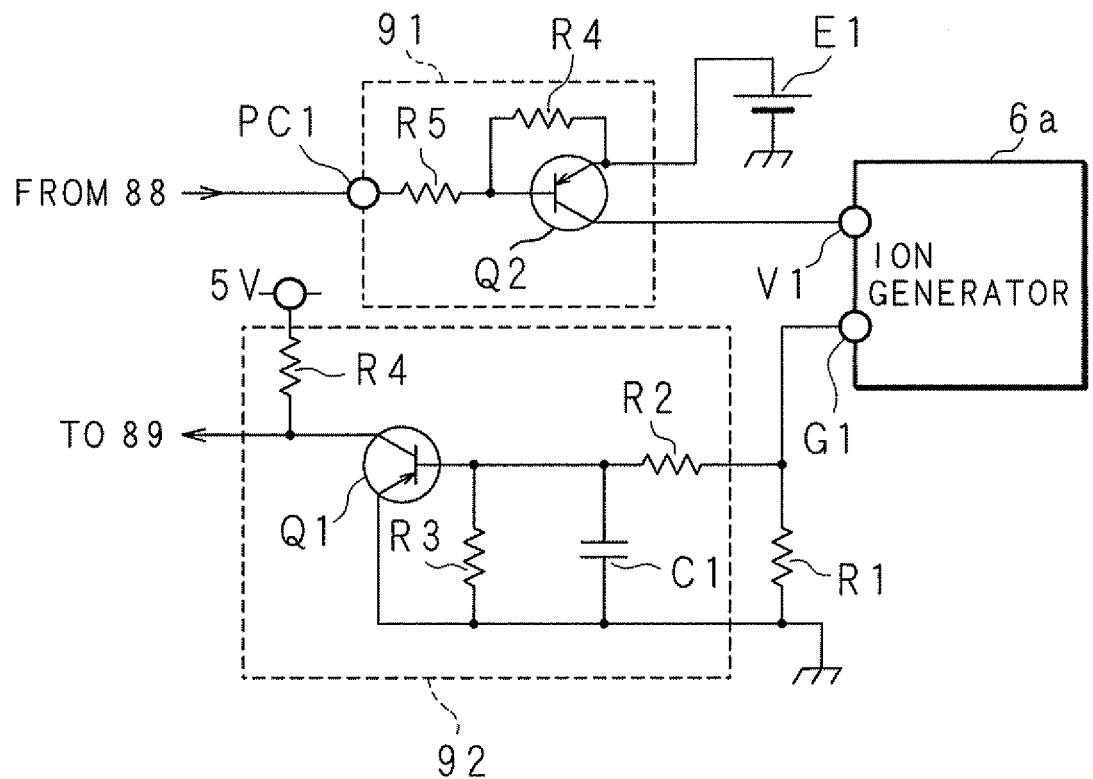
FIG. 20 is a circuit view illustrating a configuration example of an ion generator driving circuit and driving current detecting circuit connected to an ion generator.

FIG. 20 is a circuit view illustrating a configuration example of the ion generator driving circuit 91 and the driving current detecting circuit 92 connected to the ion generator 6a. The same applies to the ion generator driving circuits 91, 91, 91 and the driving current detecting circuits 92, 92, 92 connected to the ion generators 6b, 6c and 6d, respectively.

The ion generator driving circuit 91 includes a PNP transistor Q2 with the emitter and collector thereof connected to the positive electrode of a direct-current power supply E1 and a power input V1. A resistance R4 is connected between the base and emitter of the PNP transistor Q2, while a resistance R5 is connected between the base and the control input PC1 of the PNP transistor Q2.

The driving current detecting circuit 92 includes a resistance R2 with one end thereof being connected to the connecting point of the resistance R1 and the ground input G1, the other end of the resistance R2 being connected to one end of each of a condenser 1 and a resistance R3, whose other ends are connected to the ground potential, and to the base of an grounded-emitter NPN transistor Q1. The collector of the NPN transistor Q1 is connected to the input side of the input interface 89 as a detection output, and is also connected to the one end of the resistance R4, whose other end is connected to the DC5V power supply, and is pulled up.

Note that an A/D converter may alternatively be provided instead of the PNP transistor Q1 while the voltage output from the other end of the resistance R2 is integrated by a condenser, whose one end is connected to the ground potential, and is input to the A/D converter so that a digitized voltage value may be detected.

In FIG. 20, when the output of the output interface 88 becomes "L" while the negative-logic control input PC1 is turned on, base current flows in the PNP transistor Q2, so that the power input V1 of the ion generator 6a is connected to the positive electrode of the direct-current power supply E1 via the emitter and collector of the PNP transistor Q2. Thus, the ion generator 6a is driven so that the driving current flows into the ground potential from the ground terminal G1 via the resistance R1. In such a case, since the voltage emerged at both ends of the resistor R1 is divided by the resistances R2 and R3 and is applied to the base of the NPN transistor Q1, the NPN transistor Q1 is turned on when the driving current is equal to or higher than a given value, making the collector indicate "L." The input interface 89 is configured to take in the "L" indicated by the collector as a negative-logic detection signal (ON).

Figure 21:
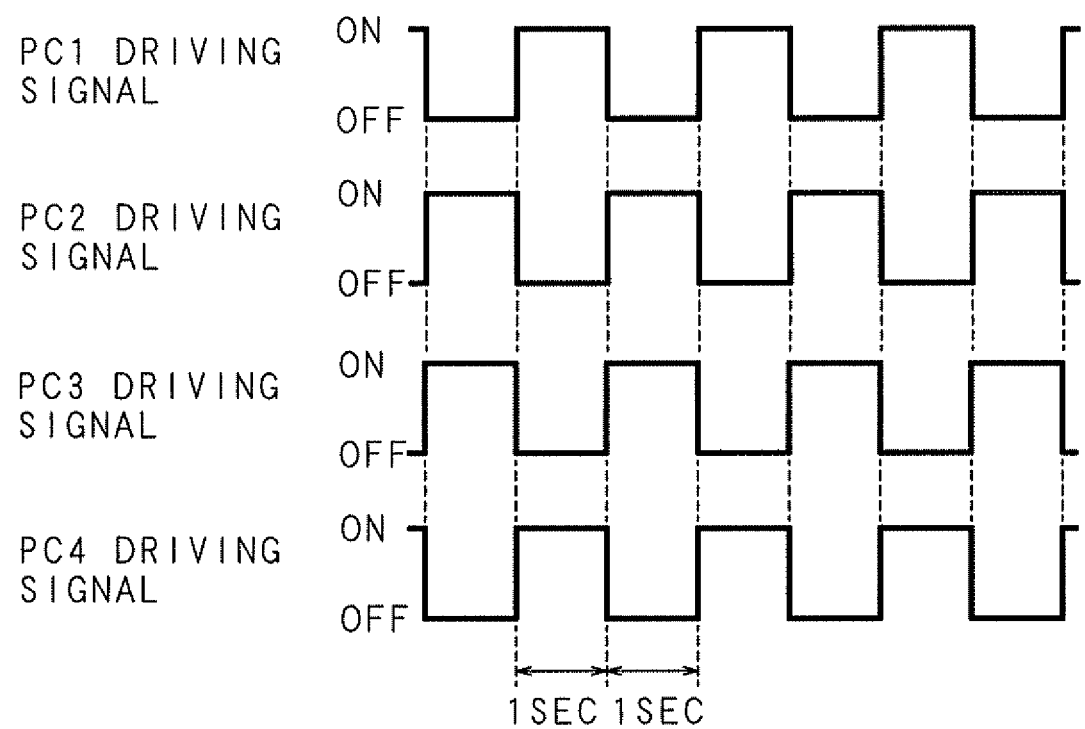
FIG. 21 is a timing chart of a driving signal input from respective output interfaces to control inputs.

FIG. 21 is a timing chart of driving signals input from the output interfaces 88, 88, 88, 88 to the control inputs PC1, PC2, PC3, PC 4, respectively. The driving signals input to the control inputs PC1 and PC2 alternately repeat "on" for one second and "off" for one second at 50% duty cycle, while the driving signals input to the control inputs PC1, PC4 and to the control inputs PC2, PC3 repeat "on" and "off" in the same phase. This makes the ion generator driving circuits 91, 91, 91, 91 alternately connect and disconnect the power supply to the respective ion generators 6a, 6d, 6b and 6c every other second. Hence, the ion generators 6a, 6d and ion generators 6b, 6c are alternately driven every other second.

Though the control inputs PC1, PC3 and the control inputs PC2, PC4 are so set as to avoid overlapping of the "on" and "off" periods, it is not limited thereto. The "on" or "off" periods may be overlapped with each other.

Figure 22:
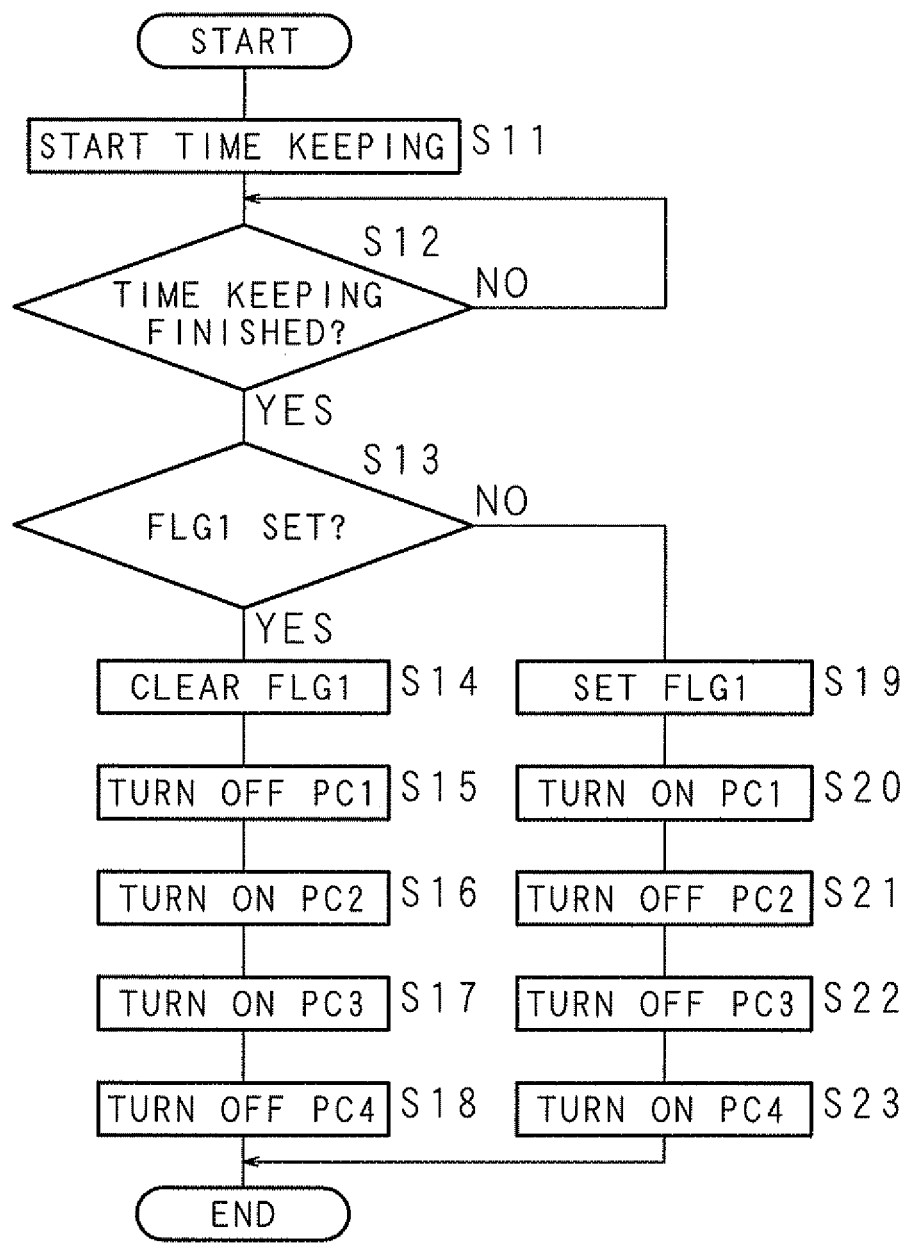
FIG. 22 is a flowchart illustrating a processing procedure of CPU that drives ion generators.

FIG. 22 is a flowchart illustrating a processing procedure of the CPU 81 that drives ion generators 6a, 6b, 6c and 6d. The processing below is executed as needed in accordance with a control program stored in the ROM 82 in advance, and is executed again every time the processing is terminated. Note that the contents of FLG1 indicating the phase of on/off are stored in the RAM 83.

The CPU 81 makes the timer 84 start keeping time for one second (step S11). The time kept is not limited to one second, but may also be 0.5 seconds, 1.5 seconds or the like. Subsequently, the CPU 81 determines whether or not the timer 84 has finished the time keeping (step S12). If it is determined that the time keeping is not finished (NO at step S12), the CPU 81 waits until the timer 84 finishes time keeping. If it is determined that the time keeping is finished (YES at step S12), the CPU 81 determines whether or not FLG 1 is set (step S13).

If it is determined that FLG 1 is set (YES at step S13), the CPU 81 clears the FLG 1 (step S14) and inverts it. Subsequently, the CPU 81 turns off the output of one output interface 88 to turn off the control input PC1 of the ion generator driving circuit 91 (step S15). Likewise, the CPU 81 turns on the control input PC2 (step S16) and turns on the control input PC3 (step S17), while it turns off the control input PC4 (step S18) and terminates the processing.

If it is determined that FLG1 is not set at step S13 (NO at step S13), the CPU 81 sets the FLG 1 (step S19). Subsequently, the CPU 81 turns on the output of one output interface 88 and turns on the control input PC1 of the ion generator driving circuit 91 (step S20). Likewise, the CPU 81 turns off the control input PC2 (step S21) and turns off the control input PC3 (step S22), while it turns on the control input PC4 (step S23) and terminates the processing.

Figure 23:
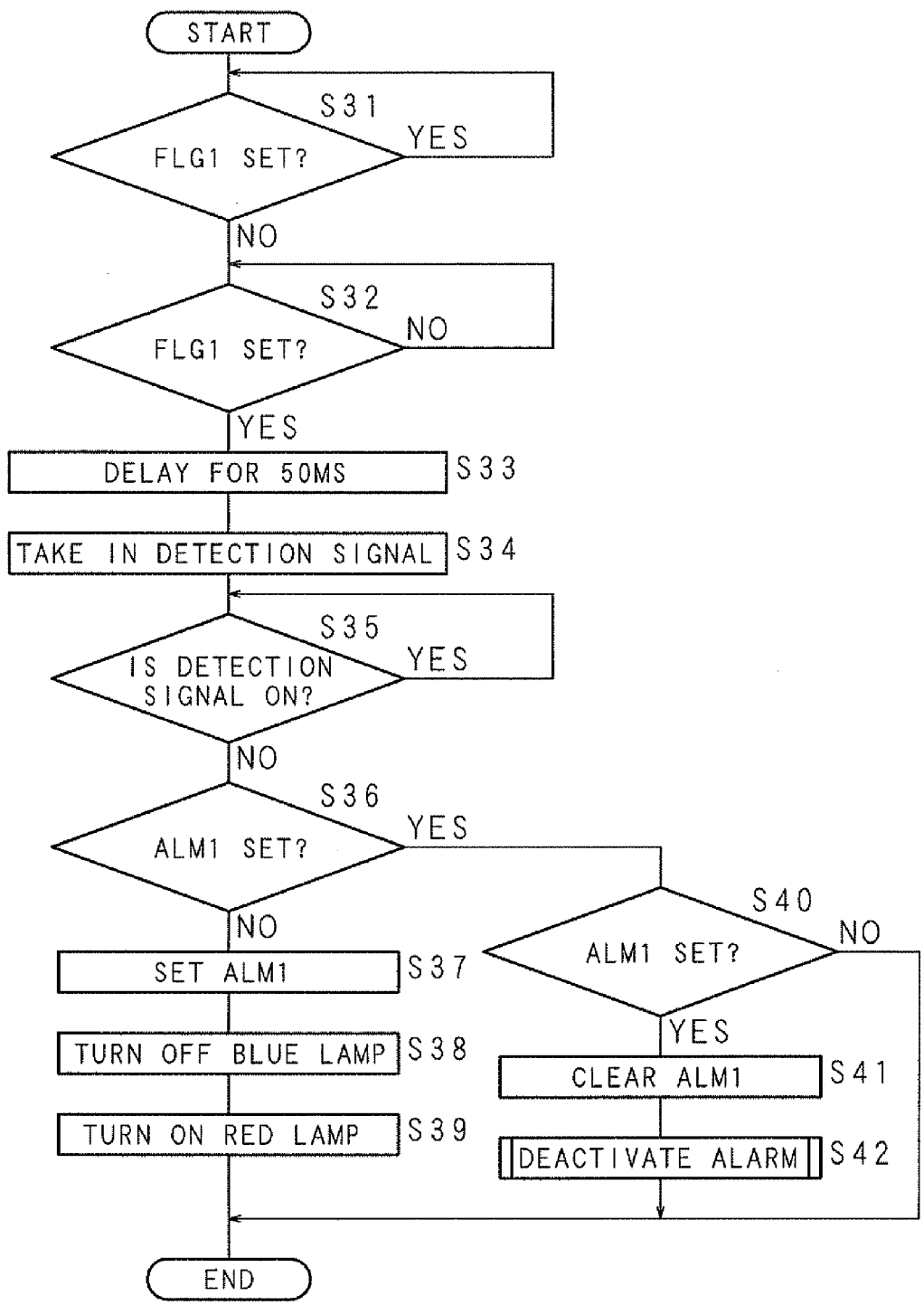
FIG. 23 is a flowchart illustrating a processing procedure of CPU that detects abnormality in driving current of an ion generator and outputs a warning.

FIG. 23 is a flowchart illustrating a processing procedure of the CPU 81 that detects abnormality in the driving current of the ion generator 6a and outputs a warning. The processing below is executed as appropriate (e.g. in a ten-minute cycle) in accordance with a control program stored in the ROM 82 in advance. Note that the cycle of executing is not limited to ten minutes, but may also be an arbitrary time. The contents of ALM1 and FLG1 are stored in the RAM 83.

The CPU 81 determines whether or not the FLG1 stored in the RAM 83 is set, i.e. whether or not the control input PC1 is turned on, in order to detect the state where the ion generator 6a is not being driven (step S31). If it is determined that the FLG1 is set (YES at step S31), the CPU 81 waits until the FLG1 is cleared. If it is determined that the FLG1 is not set (NO at step S31), the CPU 81 determines whether or not the FLG1 stored in the RAM 83 is set in order to detect the state where the ion generator 6a is being driven (step S32). If it is determined that the FLG1 is not set (NO at step S32), the CPU 81 waits until the FLG1 is set.

If it is determined that the FLG1 is set, i.e. the control input PC is raised (YES at step S32), the CPU 81 delays the processing for 50 ms, for example (step S33). The delay for 50 ms is to wait until a detection signal, which will be described later, is stabilized, and is not limited to 50 ms. Subsequently, the CPU 81 takes in the detection signal of the driving current detecting circuit 92 from the input interface 89 (step S34), and determines whether or not the obtained detection signal is on (step S35). If it is determined that the signal is not on (NO at step S35), the CPU 81 determines whether or not the ALM1 which is a flag indicating detection of abnormality has already been set (step S36).

If it is determined that the ALM1 is set (YES at step S36), the CPU81 assumes that there is a continuing abnormality and terminates the processing. If it is determined that the ALM1 is not set (NO at step S36), the CPU 81 newly sets the ALM1 (step S37) and turns off a blue lamp on the display section 86 (step S38) while it turns off a red lamp indicating a warning (step S39) and terminates the processing.

If it is determined that the detection signal is on at the step S35 (YES at step S35), the CPU 81 determines whether or not the ALM1 has already been set (step S40). If it is determined that the ALM1 is not set (NO at step S40), the CPU 81 terminates the processing. If it is determined that the ALM1 has already been set (YES at step S40), the CPU 81 clears the ALM1 so as to deactivate the warning (step S41), calls up and executes a subroutine for alarm deactivation (step S42), and terminates the processing.

Since a similar manner applies to the flowchart for detecting abnormality in the driving current of the ion generator 6d to output a warning, detailed description thereof will not be repeated. Here, the ALM1 is replaced by an ALM4.

For the flowchart for detecting abnormality of the driving current of the ion generators 6b, 6c to output a warning, a change is additionally made to determine whether or not the FLG1 is cleared at the steps S31 and S32. Here, the ALM1 is replaced by ALM2 and ALM3. Note that the contents of the ALM2, ALM3 and ALM4 are stored in the RAM 83.

Figure 24:
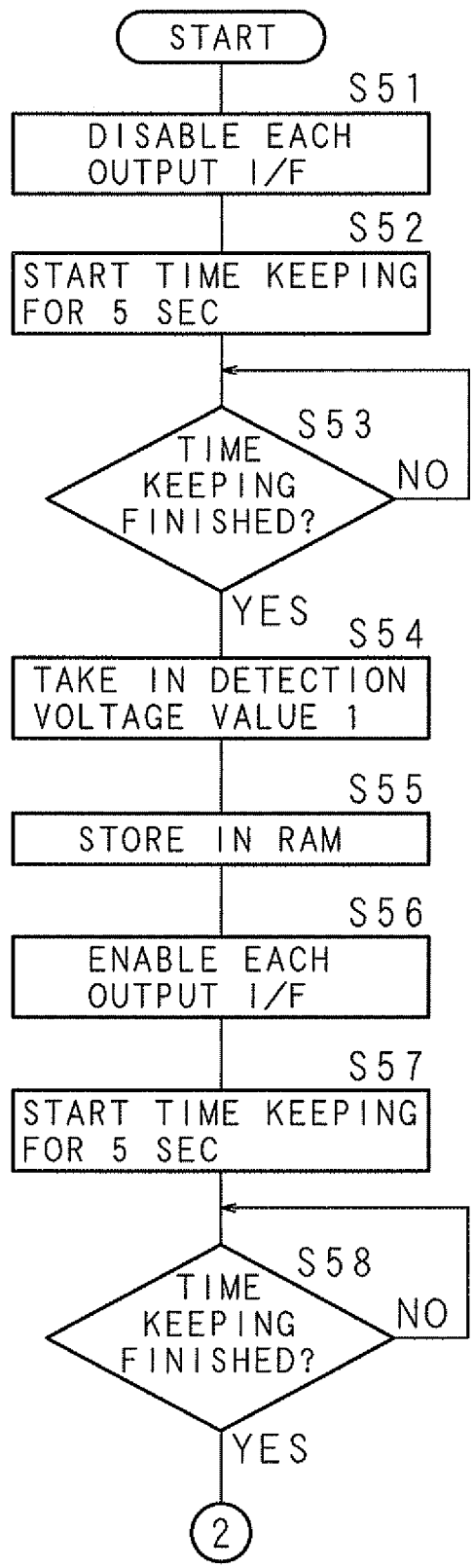
FIG. 24 is a flowchart illustrating a processing procedure of CPU that detects an abnormality in the amount of generated ions and outputs a warning.
Figure 25:
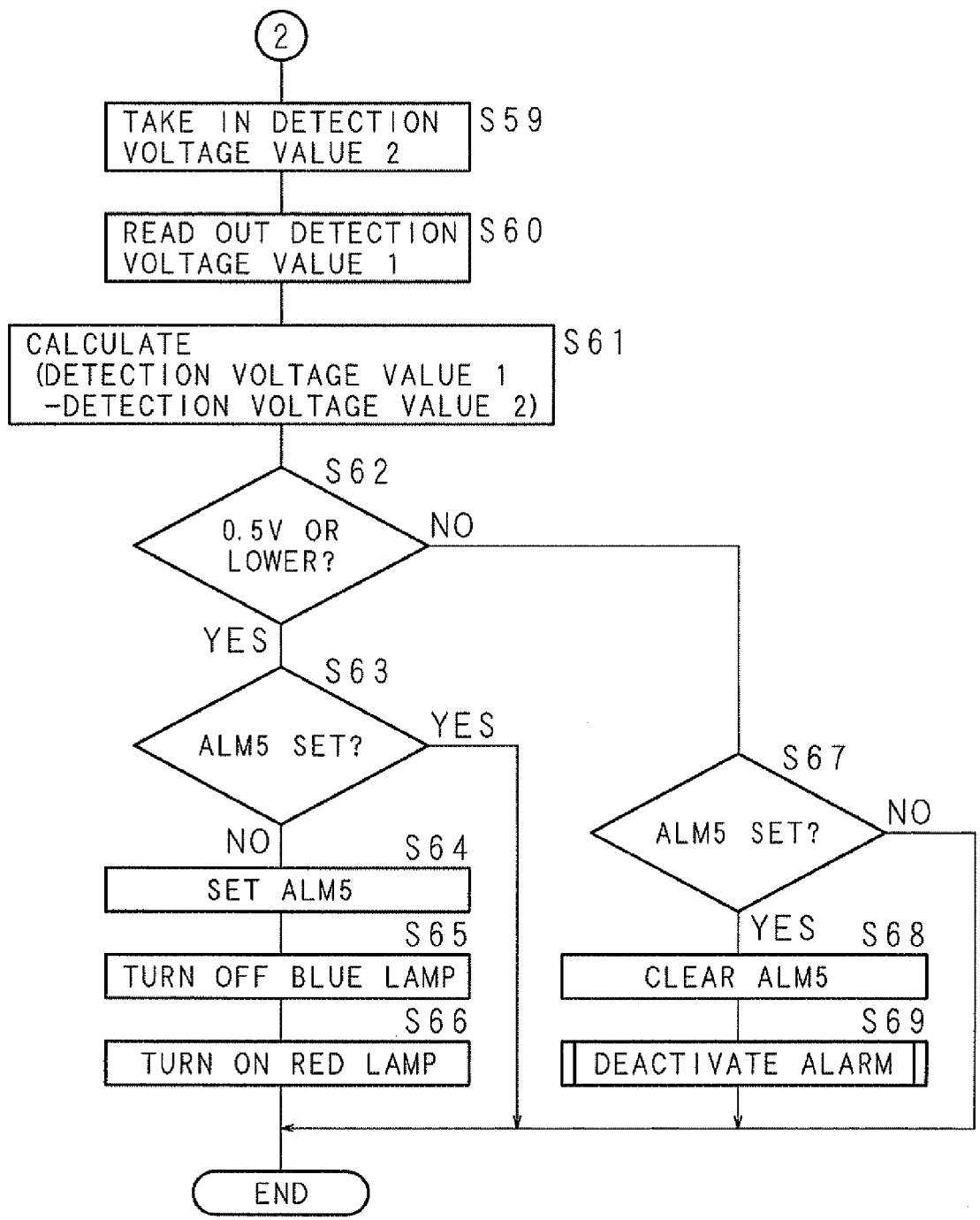
FIG. 25 is a flowchart illustrating a processing procedure of CPU that detects an abnormality in the amount of generated ions and outputs a warning.

FIGS. 24 and 25 show flowcharts illustrating a processing procedure of the CPU 81 that detects an abnormality in the amount of generated ions and outputs a warning. The processing below is executed as appropriate (e.g. in ten-minute cycle), when the above-described processing shown in FIG. 23 is not executed, in accordance with a control program stored in the ROM 82 in advance. Note that the cycle of executing is not limited to ten minutes, but may be an arbitrary time. Moreover, an ALM5 is stored in the RAM 83.

The CPU 81 forces, prior to measurement of the amount of ions, the output interfaces 88, 88, 88, 88 to be in a disable (nonoperational) state (step S51) so that the control inputs PC1, PC2, PC3 and PC4 are not turned on. Subsequently, the CPU 81 makes the timer 84 start keeping time for five seconds (step S52) and determines whether or not the timer 84 finishes the time keeping (step S53). The five seconds here is the time for waiting recovery of the potential of the ion sensor 64, and not limited thereto. If it is determined that the time keeping is not finished (NO at step S53), the CPU 81 waits until the timer 84 finishes the time keeping.

If it is determined that the time keeping is finished (YES at step S53), the CPU 81 takes in the voltage value detected by the ion detecting circuit 65 as a detection voltage value 1 (step S54), and stores the taken value in the RAM 83 (step S55). Subsequently, the CPU 81 makes the output interfaces 88, 88, 88, 88 in an enable (operational) state (step S56) so that the control inputs PC1, PC2, PC3 and PC4 are turned on and off by the processing in FIG. 22 described above.

Next, the CPU 81 makes the timer 84 start time keeping (step S57) and determines whether or not the timer 84 has finished time keeping (step S58). The five seconds here is the time for waiting until the detected voltage value reaches a steady-state value, and is not limited to five seconds. If it is determined that the time keeping is not finished (NO at step S58), the CPU 81 waits until the timer 84 finishes time keeping. If it is determined that the time keeping has been finished (YES at step S58), the CPU 81 takes in the voltage value detected by the ion detecting circuit 65 as a detection voltage value 2 (step S59).

Subsequently, the CPU 81 reads out the detection voltage value 1 from the RAM 83 (step S60), subtracts the obtained detection voltage value 2 from the read-out detection voltage value 1 (step S61), and determines whether or not the calculated value is equal to or lower than 0.5V (step S62). If it is determined that the value is equal to or lower than 0.5V (YES at step S62), the CPU 81 determines whether or not the ALM5 which is a flag indicating detection of abnormality has already been set (step S63).

If it is determined that the ALM5 has been set (YES at step S63), the CPU 81 assumes that no abnormality has been detected and terminates the processing. If it is determined that the ALM5 has not been set (NO at step S63), the CPU 81 newly sets the ALM 5 (step S64) and turns off a blue lamp on the display section 86 (step S65) while it turns on a red lamp indicating a warning (step S66) and terminates the processing.

If it is determined that the value is not equal to or lower than 0.5V (NO at step S62), the CPU 81 determines whether or not the ALM5 has already been set (step S67). If it is determined that the ALM5 has not been set (NO at step S67), the CPU 81 terminates the processing. If it is determined that the ALM5 has already been set (YES at step S67), the CPU 81 clears the ALM5 in order to deactivate a warning (step S68), calls up and executes a subroutine for alarm deactivation (step S69), and terminates the processing.

Figure 26:
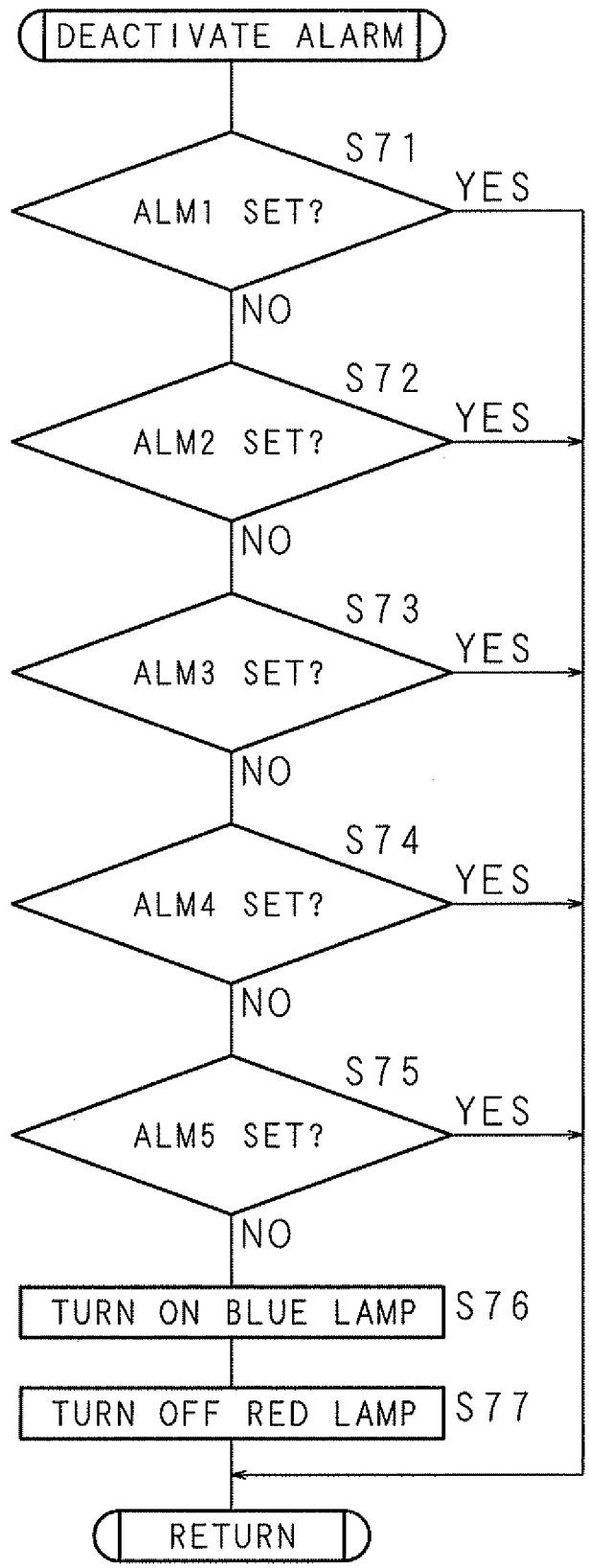
FIG. 26 is a flowchart illustrating a processing procedure of CPU concerning a subroutine for alarm deactivation.

FIG. 26 is a flowchart illustrating a processing procedure of the CPU 81 concerning a subroutine for alarm deactivation. When the subroutine for alarm deactivation is called up, the CPU 81 determines whether or not the ALM1 is set (step S71). If it is determined that the ALM1 is set (YES at step S71), the CPU 81 terminates the processing without deactivation of alarm and performs a return. If it is determined that the ALM1 is not set (NO at step S71), the CPU 81 determines whether or not the ALM2 is set (step S72).

If it is determined that the ALM2 is set (YES at step S72), the CPU81 terminates the processing without deactivation of alarm and performs a return. If it is determined that the ALM2 is not set (NO at step S72), the CPU 81 determines whether or not the ALM3 is set (step S73). If it is determined that the ALM3 is set (YES at step S73), the CPU 81 terminates the processing without deactivation of alarm and performs a return.

If it is determined that the ALM3 is not set (NO at step S73), the CPU 81 determines whether or not the ALM4 is set (step S74). If it is determined that the ALM4 is set (YES at step S74), the CPU 81 terminates the processing without deactivation of alarm and performs a return. If it is determined that the ALM4 is not set (NO at step S74), the CPU 81 determines whether or not the ALM5 is set (step S75).

If it is determined that the ALM5 is set (YES at step S75), the CPU 81 terminates the processing without deactivation of alarm and performs a return. If it is determined that the ALM5 is not set (NO at step S75), the CPU 81 turns on a blue lamp of the display section 86 (step 76) while it turns off a red lamp indicating a warning (step 77) and performs a return. This deactivates the warning.

FIG. 27 is a table illustrating measurement examples of average ion concentrations in a certain room in the case where two or four of the ion generators 6a, 6b, 6c and 6d are used and where the polarity and energized time of the ion generating sections 61 and 62 are changed. In the table, A, B, C and D correspond to the ion generators 6a, 6b, 6c and 6d, respectively. Moreover, "+" and "−" correspond to the ion generating sections 61 and 62, respectively. In the cases 1, 2 and 4, the positive ion generating sections 61 are arranged to be facing each other in the direction approximately perpendicular to the air-flowing direction in FIG. 18. In the case 5, the negative ion generating sections 62 are arranged to be facing each other in the above-described direction. In the case 3, the positive ion generating section 61 and the negative ion generating section 62 are arranged to be facing each other in the above-described direction.

For the energized time, the ion generating sections are constantly on in the case 1, while they repeat "on" for one second and "off" for one second in a two-second cycle in the cases 2, 3, 4 and 5. Moreover, a set of ion generators facing each other in the above-described direction are alternately turned on/off in the cases 2 and 5, while the set of ion generators are turned on/off in the same phase in the cases 3 and 4. FIG. 27 shows that, in the case 5 (i.e. the same arrangement as FIG. 18), the average ion concentration of 52,000 to 52,400/cm$^3$, which is approximately the same as the case 1 where two ion generating sections are constantly on, can be obtained. In the case 5, it is possible to double the operational lifetime of the ion generators 6a, 6b, 6c and 6d compared the case 1. It is confirmed that the configuration of case 5 allows the concentration of ions discharged together with the air to be increased to approximately 7,000 ions/cm$^3$ in a regular room.

As described above, according to the present embodiment, the joint wall, joint section and ducts divide the air suctioned from the suction port from two ion generators, specifically arranged for each engagement hole, to each engagement hole. This causes overlapping of ions generated by the ion generators specific to each engagement hole, suppressing mutual interference. Therefore, highly-concentrated ions can be generated.

Moreover, two ion generators specific to one engagement hole are energized in phases different from each other. This reduces the percentage of ions generated from the two ion generators in an overlapped time. Hence, the percentage of interference by ions generated from the two ion generators can be reduced.

Furthermore, the two ion generators specific to one engagement hole are alternately energized. Accordingly, the ions can be generated from two ion generators without overlapping in time. Hence, interference by ions generated from the two ion generators can be suppressed.

Furthermore, the two ion generators specific to one engagement hole is energized with an equal duty. Hence, the operational life of the two ion generators can be doubled.

Furthermore, for the two sets of ion generators arranged next to each other to form a set, the air suctioned from the suction port is divided from one and the other of each set to one and the other of the two discharge ports. Also, each set of the ion generators are alternately energized with an equal duty. This allows the operational lifetime of all the ion generators to be doubled. Moreover, when the ion generators are arranged next to each other so as to have the fluxes of the transformers of ion generators are interlinked with each other, the ion generators can be prevented from electromagnetically interfering with each other.

Furthermore, when the voltage value detected by the ion detecting circuit corresponds to the amount of ions detected by the ion sensor and the voltage value is equal to or lower than 0.5V, the red lamp on the display section is turned on to output a warning. Therefore, reliability is increased and thus the apparatus may be made suitable to continuous operation for professional use, for example.

Furthermore, the ion sensor is arranged in the proximity of an ion generating section, close to an engagement hole or at a part of a housing to detect the amount of ions. Therefore, the portion for which the amount of ions is detected may flexibly be adapted in accordance with the different uses and/or purposes.

Furthermore, when the driving current of an ion generator becomes equal to or lower than a given value so that the detection signal of the driving current detecting circuit is turned off during the period in which the ion generator is being energized, the red lamp on the display section is turned on to output a warning. Hence, normality of the ion generator can easily be recognized, further increasing the reliability.

Though, in the present embodiment, the ions generated by two ion generators are blown out from one engagement hole together with the air, it is not limited thereto. It may also be possible for ions generated by three or more ion generators are blown out from one engagement hole together with the air. Moreover, the number of engagement holes is not limited to two, but may also be three or more.

Furthermore, though the detection signal of the driving current detecting circuit is detected during the period in which the ion generator is energized, it is not limited thereto. The detection signal may also be detected based on the average driving current including the current flown in the period in which the ion generator is not energized.

Furthermore, though the red lamp on the display section is turned on as a warning, it is note limited thereto. A buzzer may be provided to output an alarming sound, or a voice synthesizing circuit and a speaker may be provided to output an alarming voice.

What is claimed is:

1. An ion generating apparatus, comprising:
   a plurality of ion generators that generate ions;
   a circuit operatively connected to the plurality of ion generators, the circuit energizing the plurality of ion generators in different phases at an equal duty,
   a plurality of discharge ports that discharge ions together with suctioned air; and
   a diversion body that divides and separates air toward each of the discharge ports.

2. The ion generating apparatus according to claim 1, comprising:
   the plurality of discharge ports comprises two discharge ports; and
   the plurality of ion generators comprises two sets of ion generators, wherein each set includes a plurality of ion generators arranged in series.

3. The ion generating apparatus according to claim 1, comprising:
   a detection section that detects an amount of ions;
   a determination section that determines whether or not the amount of ions detected by the detection section is equal to or lower than a given amount; and
   a warning section for outputting a warning when the amount of ions is equal to or lower than the given amount.

4. The ion generating apparatus according to claim 3, wherein the detection section detects the amount of ions at a portion where ions are generated, a portion where ions are discharged or a given portion outside.

5. The ion generating apparatus according to claim 1, comprising:
   a current detection section that detects current flowing in one ion generator of the plurality of ion generators; and
   a current determination section that determines whether or not a current value detected by the current detection section is equal to or higher than a given value when the one ion generator is energized, wherein
   the warning section outputs a warning when the current determination section determines that the current value is less than the given value.

6. The ion generating apparatus according to claim 2,
   wherein the two sets of ion generators include a first set of ion generators and a second set of ion generators, and
   wherein the two discharge ports include a first discharge port and a second discharge port,
   the diversion body dividing suctioned air from the first and second ion generators and respectively directing the divided suctioned air to the first and second discharge ports, such that the ions generated by the first ion generator are discharged only by the first discharge port and the ions generated by the second ion generator are discharged only by the second discharge port.

* * * * *